US007759542B2

(12) United States Patent
Chen et al.

(10) Patent No.: US 7,759,542 B2
(45) Date of Patent: Jul. 20, 2010

(54) GLYCINE N-METHYLTRANSFERASE (GNMT) ANIMAL MODEL AND USE THEREOF

(75) Inventors: Yi-Ming Chen, Taipei (TW); Shih-Ping Liu, Taipei (TW)

(73) Assignee: National Yang-Ming University, Taipei (TW)

( * ) Notice: Subject to any disclaimer, the term of this patent is extended or adjusted under 35 U.S.C. 154(b) by 0 days.

(21) Appl. No.: 11/832,304

(22) Filed: Aug. 1, 2007

(65) Prior Publication Data

US 2009/0035290 A1    Feb. 5, 2009

(51) Int. Cl.
*A01K 67/027* (2006.01)
*G01N 33/00* (2006.01)
*C12N 5/00* (2006.01)
(52) U.S. Cl. .............................. 800/18; 800/3; 435/354
(58) Field of Classification Search .................... 800/18, 800/3; 435/354; 424/94.5
See application file for complete search history.

(56) References Cited

U.S. PATENT DOCUMENTS 5,464,764 A * 11/1995 Capecchi et al. ................ 435/6

OTHER PUBLICATIONS

Holschneider et al., Int J. Devl. Neuroscience 18:615-618, 2000.*
URL: http://www.informatics.jax.org, MGI:3639796.*
Schalkwyk et al., Genes Brain Behav, 6:299-303, 2007; Abstract.*
Schoonjans et al Stem Cells, 2003; 21:90-97.*
Luka et al Transgenic Res. Jun. 2006;15(3):393-7.*
Luke et al Hum Genet. Jan. 2002;110(1):68-74.*
Aoyama, T. et al, Five of 12 Forms of Vaccinia Virus-Expressed Human Hepatic Cytochrome P450 Metabolically Activate Aflatoxin B1, Journal, Jun. 1990, vol. 87, pp. 4790-4793 Proc. Natl. Acad.Sci. USA.
Bressac,B. et al., Selective G to T Mutations of p53 Gene in Hepatocellular Carcinoma from Southern Africa, Journal, 1991, pp. 429-431,350, Letters to Nature; HSU,I.C. et al., Mutational Hotspot in the p53 Gene in Human Hepatocellular Carcinomas, Journal, 1991, pp. 427-428, 350, Letters to Nature.
Hsieh, L.L., et al, Immunological Detection of Aflatoxin B1-DNA Adducts Formed in Vivo, Journal, Nov. 1988, pp. 6328-6331, 48, Cancer Research.
Tseng, T.L., et al, Genotypic and Phenotypic Characterization of a Putative Tumor Susceptibility Gene, GNMT, in Liver Cancer, Journal, Feb. 2003, pp. 647-654, 63, Cancer Research.
Chen, S.Y., et al, Glycine N-Methyltransferase Tumor Susceptibility Gene in the Benzo(a)pyrene-Detoxification Pathyway, Journal, May 2004, pp. 3617-3623, 64, Cancer Research.
Case, G.L., et al., Evidence for S-adenosylmethionine Independent Catabolism of Methionine in the Rat, Journal, 1976, pp. 1721-1736, 106, Journal of Nutrition.
Chen, C.J.,et al, Aflatoxin B1 DNA Adducts in Smeared Tumor Tissue from Patients with Hepatocellular Carcinoma, Journal, 1992, pp. 1150-1155, 16, Hepatology.
Croy,R.G., et. al., Identification of the Principal Aflatoxin B1-DNA Adduct Formed in Vivo in Rat Liver, Journal, 1978, pp. 1745-1749, 75, Proc. Natl. Acad. Sci. USA.
Degen, G.H., et al,The Major Metabolite of Aflatoxin B1 in the Rat is a Glutathione Conjugate, Journal, 1978, pp. 236-255, 22, Chem. Biol. Interact.
Dirr, H. W., et al, Intracellular Aflatoxin B1-Binding Proteins in Rat Liver, Journal 1987, pp. 297-302, 14, Biochemistry International.
Mode, A., et al, Sex and the Liver-A Journey Through Five Decades, Journal, 2006, pp. 197-207, 38, Drug Metabolism Reviews.
Forrester, L.M., et al., Evidence for Involvement of Multiple Forms of Cytochrome P-450 in Aflatoxin B1 Metabolism in Human Liver, Journal, 1990, pp. 8306-8310, 87, Proc. Natl. Acad. Sci. USA.
Chen,Y.M., et al, Genomic Structure, Expression, and Chromosomal Localization of the Human Glycine N-Methyltransferase Gene, Journal, 2000, pp. 43-47, 66, Genomics.
Ghebranious, N., et al, Hepatitis B Injury, Male Gender, Aflaxtoxin, and p53 Expression Each Contribute to Hepatocarcinogenesis in Transgenic Mice, Journal, 1998, 27, Hepatology.
Chen,Y.M., et al, Characterization of Glycine-N-Methyltransferase-Gene Expression in Human Hepatocellular Carcinoma, Journal, 1998, pp. 787-793, 75, IntJCancer.
Kerr, Sylvia J., Competing Methyltransferase Systems, Journal, 1972, pp. 4248-4252, 247, Journal of Biological Chemistry.
Heady, J.E., et al, Purification and Characterization of Glycine N-Methyltransferase, Journal, 1973, pp. 69-72, 248, Journal of Biological Chemistry.
Ogawa, H., et al, Purification and Properties of Glycine N-Methyltransferase from Rat Liver, Journal, 1982, pp. 3447-3452, 257, Journal of Biological Chemistry.
Raha, A., et al, Rat Liver Cytosolic 4 S Polycyclic Aromatic Hydrocarbon-binding Protein is Glycine N-Methyltransferase, Journal, 1994, pp. 5750-5756, 269, Journal of Biological Chemistry.
Kensler, T.W., et al, Modulation of Aflatoxin Metabolism, Aflatoxin N7-guanine Formation, and Hepatic Tumorigenesis in Rats Fed Ethoxyquin: Role of Induction of Glutathione S-Transferases, Journal, 1986, pp. 3924-3931, 46, Cancer Research.
Koser, P.L. et al, Association of the Induction of Aflatoxin B1-4-Hydroxylase with the Transcriptional Activation of Cytochrome P3-450 Gene, Journal, 1988, pp. 12584-12595, 263, Journal of Biological Chemistry.
Liang, P., et al, Differential Display and Cloning of Messenger RNAs from Human Breast Cancer versus Mammary Epithelial Cells, Journal, 1992, pp. 6966-6968, 52, Cancer Research.
Liu, H. H., et al, Characterization of Reduced Expression of Glycine N-Methyltransferase in Cancerous Hepatic Tissues Using Two Newly Developed Monoclonal Antibodies, Journal, 2003, pp. 87-97, Journal Biomedical Science.

(Continued)

*Primary Examiner*—Deborah Crouch
*Assistant Examiner*—Anoop Singh
(74) *Attorney, Agent, or Firm*—WPAT, P.C.; Anthony King

(57) ABSTRACT

The present invention is a new type of Glycine N-methyltransferase (GNMT) knockout mice model. This model can be applied to screen drug, test of treatment and search for diagnostic marker of hepatocellular carcinoma (HCC), glycogen storage disease, liver dysplasia, fatty liver and other liver disease.

4 Claims, 14 Drawing Sheets

OTHER PUBLICATIONS

McLean, M, et al, Cellular Interactions and Metabolism of Aflatoxin: An Update, Journal, 1995, pp. 163-192, 65, Pharmacol. Ther. vol. 65, Elsvier Science Ltd., Great Britain.

Waxman, D.J., et al, Growth Hormone Regulation of Sex Dependent Liver Gene Expression, Journal, 2006, pp. 2613-2629, The Endocrine Society, USA.

Morris, G.M., et al, Automated Docking Using a Lamarck Genetic Algorithm and an Empirical Binding Free Energy Function, Journal, 1998, pp. 1639-1662, The Scripps Research Institute, La Jolla, CA.

Pascale, R.M., et al., Genomic Abnormalities in Hepatocarincoghenesis. Implications for a Chemopreventive Strategy, Journal, 1993, 131341-1356, vol. 13, Anticancer Research.

Cook, R.J., et al., Glycine N-methytransferase is a Folate Binding Protein of Rat Liver Cytosol, Journal, 1984, 3631-3634, vol. 81, Proc. Natl. Acad. Sci., USA.

Hayes, J.D., Contribution of the Glutathione S-Transferases to the Mechanisms of Resistance to Aflatoxin, Journal, 443-454, University Department of Clinical Chemistry.

Schafer, D.F. et al., Outbreak of Nipah-virus Infection Among Abbatoir Workers in Singapore, Journal, 1999, 1253-1257, vol. 354, The Lancet.

Swenson, D.H. et al., Aflatoxin B1, 2, 3: Evidence for Its Formation in Rat Liver in Vivo and by Human Liver Microsomes in Vitro, Journal, 1974, 1036-1043, vol. 60, Biochem. Biophys. Res. Commun.

Taggert, P. et al., Multiple Aflatoxin B1 Binding Proteins Exist in Rat Liver Cytosol, Journal, 1986, 68-72, vol. 182, Proc. Soc. Exp. Biol. Med., Philadelphia, PA.

Valera, A. et al., Transgenic Mice Overexpressing Phosphoenolpyruvate Caroxykinase Develop Non-insulin-dependent Diabetes Mellitus, vol. 91, 9151-9154, Proc. Natl. Acad. Sci. USA.

Williams, J.H. et al., Human Alatoxicosis in Developing Countries: A Review of Toxicology, Exposure, Potential Health Consequences, and Interventions, 2004, 1106-1122, vol. 80, Am. J. Clin. Nutr.

Yu, M.W. et al., Hepatitis B and C Viruses in the Development of Hepatocellular Carcinoma, 1994, 71-91, vol. 17, Crit Rev. Oncol. Hematol.

Yi-Jen Liao et al., Characterization of a glycine N-methyltransferase gene knockout mouse model for hepatocellular carcinoma: Implications of the gender disparity in liver cancer susceptibility, Int. J. Cancer, journal, 2009, p. 816-826, 124, Wiley-Liss, Inc.

\* cited by examiner

A.

B.

C.

A

B

GLYCINE N-METHYLTRANSFERASE (GNMT) ANIMAL MODEL AND USE THEREOF

FIELD OF THE INVENTION

The present invention relates to Glycine N-methyltransferase (GNMT) animal model and use thereof. The present invention also relates to the use of GNMT product in preventing or treating cancer, especially liver cancer.

BACKGROUND OF THE INVENTION

One of the most common types of human diseases throughout the world due to cell abnormalities is cancer, which is also the leading cause of death nowadays. Cancers are fully developed (malignant) tumors with a specific capacity to invade and destroy the underlying mesenchyme, i.e., local invasion. In some cases, invading tumor cells may further penetrate lymphatic vessels or blood vessels newly formed in the tumor and then may be carried to local lymph nodes or even to distant organs where they may produce secondary tumors (metastases). Tumors are usually recognized by the fact that the cells, which may arise from any tissue, are no longer responsive to at least some normal growth controlling mechanisms and hence show abnormal growth. Apart from the cancer, a tumor may merely develop locally and never become malignant, i.e., a benign tumor. Alternatively, cells of a tumor may merely have morphological appearances of cancer cells but remain in their place, i.e., an in situ tumor, although in this case the tumor may sometimes precede a cancer in situ.

There are no absolute methods for diagnosing or assessing the degree of malignancy of tumors. However, among the methods, microscopic examination of tissue is still the most reliable method for routine use. In a pathologic study, tumors can be graded by making an approximate assessment of the degree of structural dedifferentiation (anaplasia) based on histological and cytological criteria by microscopically examining sections thereof. However, on one hand, some cells may have lost their specific structural characters but still retain differentiated biochemical features, while others may still appear differentiated in structure but have lost many normal function attributes. On the other hand, a tumor is not homogeneous and may contain areas with more than one tumor grade, therefore, a developed tumor may consist of a mixed population of cells which may differ in structure, function, growth potential, resistance to drugs or X-rays and ability to invade and metastasize. The two limitations reduce the effectiveness of histological examination of tumors. In another aspect, such an examination by sampling specimens is not suitable for investigations on a large scale.

Many attempts to find absolute markers of malignancy have long been made. Other attempts to identify tumor-specific or tumor-associated proteins, either by direct measurement or by developing specific antibodies to these proteins, are still being made at the moment. They seem to be promising approaches not only in diagnosis but also in providing strategies of destroying cancer cells. A variety of substances wherein the presence or concentrations thereof in vivo may be indicative for certain cancers have been reported, such as oncofetal antigens, e.g., alpha-fetoprotein; serum proteins, e.g., ferritin; enzymes; polyamines; ectopic hormones; cell markers; receptors or tumor-associated viral antigens. However, the most commonly used method of diagnosis of cancers depends on histology rather than any of the above substances. The lack of any absolute markers is a major deficiency in studying cancer.

Recent observations provide some contemplation in searching for the substances intimately associated with carcinogenesis. Cancer is appreciated as a result of multiple gene aberrations which cause both the activation of oncogenes and inactivation of tumor suppressor genes. Further, the differential expression of those critical genes associated with oncogenesis is able to be reflected at the messenger RNA (mRNA) level in cells. For effectively screening the altered ones of interest amongst a great amount of mRNA, a powerful tool, i.e., differential display has been established to identify and isolate a small subset of genes which are differentially expressed between tumorous and normal cells (Liang et al., Cancer Research 52, 6966-6968, 1992).

Human hepatocellular carcinoma (HCC), one of the world's most common cancers, usually develops from chronic inflammatory liver disease via viral infections that induce cirrhosis and exposure to chemical carcinogens (Yu, M. W. et al., *Crit. Rev. Oncol. Hematol.* 17, 71-91, 1994; Schafer, D. F. et al., *Lancet* 353, 1253-1257, 1999; Williams, J. H. et al., *Am. J. Clin. Nutr.* 80, 1106-1122, 2004). In some areas (e.g., China and Africa) HCC is primarily caused by viral infections (HBV, HCV), food contaminated by aflatoxin B1 (AFB1), and other forms of aflatoxin ingestion (Williams, J. H. et al., *Am. J. Clin. Nutr.* 80, 1106-1122, 2004; Chen, C. J., *Hepatology* 16, 1150-1155, 1992). Aflatoxin metabolites are secondary products of *Aspergillus flavus* and *Aspergillus parasiticus* fungi under hot and humid conditions. These ubiquitous fungi affect such dietary staples as rice, corn, cassava, nuts, peanuts, chilies, and spices (McLean, M. & Dutton, M. E, *Pharmacol. Ther.* 65, 163-192, 1995). Chemicals or xenobiotics (such as AFB1) that encounter biologic systems can be altered by metabolic processes. In phase I of the detoxification pathway, cytochrome P450 isoenzymes (induced by polycyclic aromatic hydrocarbons and chlorinated hydrocarbons) add one atom of oxygen to the substrate; bioactivation is an occasional sequela (Hsieh, D. P. H., Elsevier Scientific Publishers, Amsterdam, 1986; Hsieh, D. P. H., Academic, Cambridge, 1987; Aoyama, T. et al., *Proc. Natl. Acad. Sci. U.S. A* 87, 4790-4793, 1990; Swenson, D. H. et al., *Biochem. Biophys. Res. Commun.* 60, 1036-1043, 1974). The reactive intermediate aflatoxin B1 8,9-epoxide (produced by CYP isoenzymes, shch as cytochrome P450IA2 and P450IIIA4) is carcinogenic in many animal species; its covalent binding to hepatic DNA has been shown to be a critical step in hepatocarcinogenesis (Forrester, L. M., et al., *Proc. Natl. Acad. Sci. U.S. A* 87, 8306-8310, 1990; Koser, P. L. et al., *J. Biol. Chem.* 263, 12584-12595, 1988). Phase II enzymes of primary importance belong to the GST group; these catalyze the conjugation of potentially toxic electrophiles to the GSH tripeptide, generally rendering them non-toxic (Degen, G. H. & Neumann, H. G., *Chem. Biol. Interact.* 22, 239-255, 1978; Hayes, J. D. et al., *Pharmacol. Ther.* 50, 443-472, 1991). The reactive aflatoxin B1 8,9-epoxide subsequently attacks and damages DNA. The major AFB1-DNA adduct formed in vivo is AFB1-N7-guanine (Croy, R. G. et. al., *Proc. Natl. Acad. Sci. U.S. A* 75, 1745-1749, 1978; Kensler, T. W. et al., *Cancer Res.* 46, 3924-3931, 1986). There are at least two reports indicating that AFB1 binds covalently with DNA and induces G:C to T:A transversions at the third base in codon 249 of p53—considered a hot spot for AFB1 mutagenesis (Bressac, B. et. al., *Nature* 350, 429-431, 1991; Hsu, I. C. et al., *Nature* 350, 427-428).

GNMT is an intracellular enzyme which catalyzes the synthesis of sarcosine from glycine. Through this enzyme, glycine receives a methyl group from S-adenosylmethionine (SAM) and becomes sarcosine, which can be subsequently oxidized to become glycine again by sarcosine dehydrogenase. The latter reaction will generate energy and release one carbon unit from SAM. GNMT thus plays a key role in regulating the ratio of SAM to S-adenosylhomocysteine (SAH). The properties of rat liver GNMT, such as its activity being fluctuated and correlated with the level of methionine in the diet and its inducibility with a methionine-rich diet, suggest that it also plays a crucial role in regulating tissue concentration of SAM and metabolism of methionine (Ogawa, H. et al., J. Biol. Chem., 257:3447-3452, 1982). However, GNMT was found to be merely responsible for the metabolism of 20% of total metabolized methionine in vivo (Case et al., J. Nutr. 106: 1721-1736, 1976), but this protein is abundant in liver of mature rats or mice, almost 1% to 3% of the total soluble proteins in liver (Heady et al., J. Biol. Chem., 248:69-72, 1973). Therefore, the GNMT protein may exert other important physiological functions, one of which was found to be identical to a folate-binding protein purified from rat liver cytosol (Cook, R. J. et al., Proc. Natl. Acad. Sci. USA, 81:3631-3634, 1984). Recently, Raha et al. (J. Biol. Chem., 269:5750-5756) proved that GNMT is the 4 S polycyclic aromatic hydrocarbon-binding protein which interacts with 5'-flanking regions of the cytochrome P4501A1 gene (CYP1A1).

Furthermore, as GNMT is the most abundant and efficient methyltransferase in hepatocytes, the activity of GNMT may influence other methyltransferases, e.g., the activity of tRNA methyltransferase can be blocked by GNMT (Kerr et al., J. Biol. Chem., 247:4248-4252, 1972). Results from various laboratories have indicated that lipotropic compounds, such as SAM and its precursors: methionine, choline and betaine, can prevent the development of liver tumors induced by various carcinogens in a rat or mouse model. Due to the findings that GNMT is tightly associated with the SAM level in liver cells and its enzyme activity may be activated by SAM, the GNMT may involve the chemopreventive pathway way of liver cancer (Pascale et al., Anticancer Res., 13:1341-1356, 1993).

It has been reported that diminished GNMT expression levels in both human hepatocellular carcinoma cell lines and tumor tissues (Liu, H. H. et al, *J. Biomed. Sci.* 10, 87-97, 2003; Chen, Y. M. et al., *Int. J. Cancer* 75, 787-793, 1998). Human GNMT gene is localized to the 6p12 chromosomal region and characterized its polymorphism (Chen, Y. M. et al., *Genomics* 66, 43-47, 2000). Genotypic analyses of several human GNMT gene polymorphisms showed a loss of heterozygosity in 36-47% of the genetic markers in hepatocellular carcinoma tissues (Tseng, T. L. et al., *Cancer Res.* 63, 647-654, 2003). It also reported that GNMT were involved in the benzo(a)pyrene (BaP) detoxification pathway and reduced BPDE-DNA adducts that formed in GNMT-expressing cells (Chen, S. Y. et al., *Cancer Res.* 64, 3617-3623, 2004).

Previous results indicated that multiple proteins were capable of binding aflatoxin B1 in rat liver cytosol (Taggart, P. et al., *Proc. Soc. Exp. Biol. Med.* 182, 68-72, 1986). Cytosolic proteins involved in AFB1 binding may have the potential to function in the transport, metabolism and even action of the carcinogen (Dirr, H. W. & Schabort, J. C., *Biochem. Int.* 14, 297-302, 1987).

SUMMARY OF THE INVENTION

The present invention provides a knock-out mouse whose genome is disrupted by recombination at Glycine N-methyltransferase (GNMT) gene locus so as to produce a phenotype, relative to a wild-type phenotype, comprising abnormal liver function of said mouse, wherein the disruption occurs neucleotides 547-4875 of SEQ ID No. 8.

The present invention also provides a method for screening a candidate agent for preventing or treating liver disease or disorder comprising:
(a) providing the knock-out mouse of the present invention;
(b) administering to said the knock-out mouse a candidate agent, and
(c) comparing liver function of the knock-out mouse to that of the knock-out mouse of not administered said candidate agent; wherein the agent that ameliorates liver function is selected as an agent that has effectiveness against said liver disease or disorder.

The present invention further provides a pair of prime, which is (i) SEQ ID Nos 1 and 2 or (ii) SEQ ID Nos 1 and 2.

The present invention further provides a database for regulatory genes in GNMT knock-out mouse a database for regulatory genes in GNMT knock-out mouse.

The present invention also provides a database for hepatocellular carcinoma signaling pathway genes.

The present invention further provides a method for treating or preventing disease caused by aflaoxin B1 (AFB1) in a patient subject comprising administering the patient with an effective amount of Glycine N-methyltransferase (GNMT) or plasmid including GNMT.

The present invention also provides a composition for treating or preventing disease caused by aflaoxin B1 comprising Glycine N-methyltransferase (GNMT) and pharmaceutically or food acceptable carrier.

DETAILED DESCRIPTION OF THE INVENTION

Figure 1:
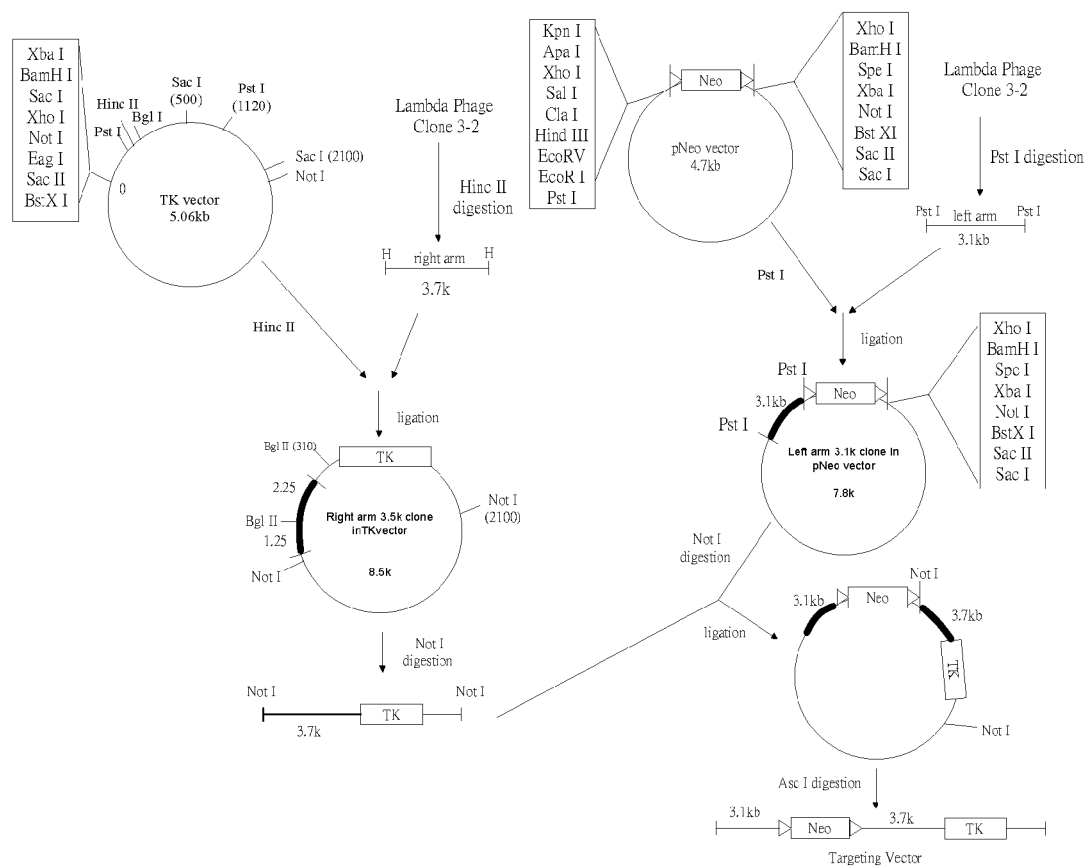
FIG. 1 shows the strategy of constructing the targeting vector.

It is surprisingly found in the present invention that the GNMT gene is differentially expressed between normal and tumorous cells with a significant distinction. An objective of the present invention is to provide a method of detecting abnormalities of cells by determining the relative levels of gene expression of GNMT. Furthermore, another objective of the present invention is to provide a method of correcting the abnormalities of cells by delivering GNMT into the abnormal cells.

Non-human transgenic animal models useful for screening psychoactive drugs are provided. The animals have genetically altered GNMT gene. Alterations to the gene include deletion or other loss of function mutations, introduction of an exogenous gene having a nucleotide sequence with targeted or random mutations, introduction of an exogenous gene from another species, or a combination thereof. The transgenic animals may be either homozygous or heterozygous for the genetic alteration.

GNMT undergoes nuclear translocation following $AFB_1$ treatment. According to the results of tests of the present invention, $AFB_1$ binds with GNMT and competes with SAM for the same binding site. Evidence was also found in support of the idea that GNMT antagonizes $AFB_1$-induced cytotoxicity by reducing $AFB_1$-DNA adduct formation and enhancing $AFB_1$-treated cell survival rate. Finally, results from GNMT transgenic mouse model showed that overexpression of GNMT exhibited protective effect against $AFB_1$ induced hepatocellular carcinoma.

The present invention provides a method for treating or prevening disease caused by aflaoxin B1 (AFB1) in a patient subject comprising administering the patient with an effective amount of Glycine N-methyltransferase (GNMT) or plasmid including GNMT.

In a preferred embodiment, the disease is hepatocellular carcinoma (HCC).

In the present method, the treatment or prevention is made by blocking formation of AFB1-DNA adducts.

For gene therapy, the plasmid can be regarded as a plasmid vaccine and could be directly administered to the body of the patient by current technology for gene therapy.

The present invention provides a knock-out mouce whose genome is disrupted by recombination at Glycine N-methyltransferase (GNMT) gene locus so as to produce a phenotype, relative to a wild-type phenotype, comprising abnormal liver function of said mouse, wherein the disruption occurs neucleotides 547-4875 of SEQ ID No. 8.

In particular, the nucleotides are GNMT exons 1-4 and a part of exon 5. The phenotype of absence of Glycine N-methyltransferase activity results from a diminished amount of mature Glycine N-methyltransferase relative to the wild-type phenotype.

In the preparation of knock-out mouse, the Glycine N-methyltransferase gene is disrupted by recombination with heterologous nucleotide sequence (such as neomycin).

The term "abnormal liver function" herein is not limited but includes elevation of S-adenosylmethionine (SAM), alanine aminotransferase (ALT) or asparate aminotransferase (AST).

Transgenic Animals

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

Transgenic animals fall into two groups, colloquially termed "knockouts" and "knockins". In the present invention, knockouts have a partial or complete loss of function in one or both alleles of the endogenous GNMT gene. Knockins have an introduced transgene with altered genetic sequence and function from the endogenous gene. The two may be combined, such that the naturally occurring gene is disabled, and an altered form introduced.

In a knockout, preferably the target gene expression is undetectable or insignificant. A knock-out of a GNMT gene means that function of the GNMT gene has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of GNMT gene. A functional knock-out may also be achieved by the introduction of an anti-sense construct that blocks expression of the native genes. "Knockouts" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knock-in" of a target gene means an alteration in a host cell genome that results in altered expression or function of the native GNMT gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or repressor.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. The introduced sequence may encode a GNMT polypeptide. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

Specific constructs of interest, but are not limited to, include anti-sense GNMT gene, which will block native GNMT expression, expression of dominant negative GNMT mutations, and over-expression of a GNMT gene. A detectable marker, such as lac Z may be introduced into the locus, where upregulation of expression will result in an easily detected change in phenotype.

A series of small deletions and/or substitutions may be made in the GNMT gene to determine the role of different exons in DNA binding, transcriptional regulation, etc. By providing expression of GNMT protein in cells in which it is otherwise not normally produced, one can induce changes in cell behavior.

DNA constructs for homologous recombination will comprise at least a portion of the GNMT gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

Accordingly, the present invention also provides a cell or cell line, which is prepared from the knock-out mouse of thepresent invention. In a preferred embodiment, the cell or cell line is an undifferentiated cell selected from the group consisting of: a stem cell, embryonic stem cell oocyte and embryonic cell.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

Drug Screening Assays

The present invention further provides a method for screening a candidate agent for preventing or treating liver disease or disorder comprising:

(i) providing the knock-out mouse of the present invention;
(ii) administering to said the knock-out mouse a candidate agent, and
(iii) comparing liver function of the knock-out mouse to that of the knock-out mouse of not administered said candidate agent; wherein the agent that ameliorates liver function is selected as an agent that has effectiveness against said liver disease or disorder.

Through use of the subject transgenic animals or cells derived therefrom, one can identify ligands or substrates that bind to, modulate, antagonize or agonize GNMT polypeptide. Screening to determine drugs that lack effect on these polypeptides is also of interest. Of particular interest are screening assays for agents that have a low toxicity for human cells.

A wide variety of assays may be used for this purpose, including in vivo behavioral studies, determination of the localization of drugs after administration, labeled in vitro protein-protein binding assays, protein-DNA binding assays, electrophoretic mobility shift assays, immunoassays for protein binding, and the like. Depending on the particular assay, whole animals may be used, or cell derived therefrom. Cells may be freshly isolated from an animal, or may be immortalized in culture. Cell of particular interest include neural and brain tissue.

The term "agent" as used herein describes any molecule, e.g. protein or pharmaceutical, with the capability of affecting the biological action of GNMT polypeptide. Generally a plurality of assay mixtures are run in parallel with different agent concentrations to obtain a differential response to the various concentrations. Typically, one of these concentrations serves as a negative control, i.e. at zero concentration or below the level of detection.

In a preferred embodiment, the agent is for preventing or treating hepatocellular carcinoma (HCC), glycogen storage disease, liver dysplasia or fatty liver.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening may be directed to known pharmacologically active compounds and chemical analogs thereof. known anti liver cancer or disease drugs include the Drugs with a significant hepatoprotective effect are of particular interest.

To prepare the knock-out mouse, the present invention also provides a pair of prime, which is (i) SEQ ID Nos 1 and 2 or (ii) SEQ ID Nos 3 and 4.

The present invention further provides a database for regulatory genes in GNMT knock-out mouse to study up-regulatory and down-regularity genes.

The present invention further provides a database for hepatocellular carcinoma signaling pathway genes comprising (a) survival and proliferation: PTEN, PI3K, Akt 1, GSK3β or β-catenin
(b) oncogenes: Cyclin D1,C-myc or C-Jun; and
(c) tumor suppressor gene: Rb or p53.

The present invention also provides a composition for treating or prevening disease caused by aflaoxin B1 comprising Glycine N-methyltransferase (GNMT) and pharmaceutically or food acceptable carrier. In a preferred embodiment, the GNMT is in dimeric or tetrameric forms.

The composition of the present invention could be applied as a supplementary additive for a dietary staple (such as rice, corn, cassaya, nut, peanut, chilies or spices).

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

To construct a targeting vector, DNA fragments digested from lambda phage clones 3-2 and 5-3 were inserted into a plasmid-pBluescrip II KS. Left arm was digested from the phage clone 5-3 by using Pst I and inserted into the pNeo vector. Right arm was digested from the phage clone 3-2 by using Hinc II and inserted into the TK vector. The fragment containing right arm and TK gene was digested by using Not I and inserted into the pNeo vector containing left arm to generate the targeting vector (FIG. 1).

Figure 2:
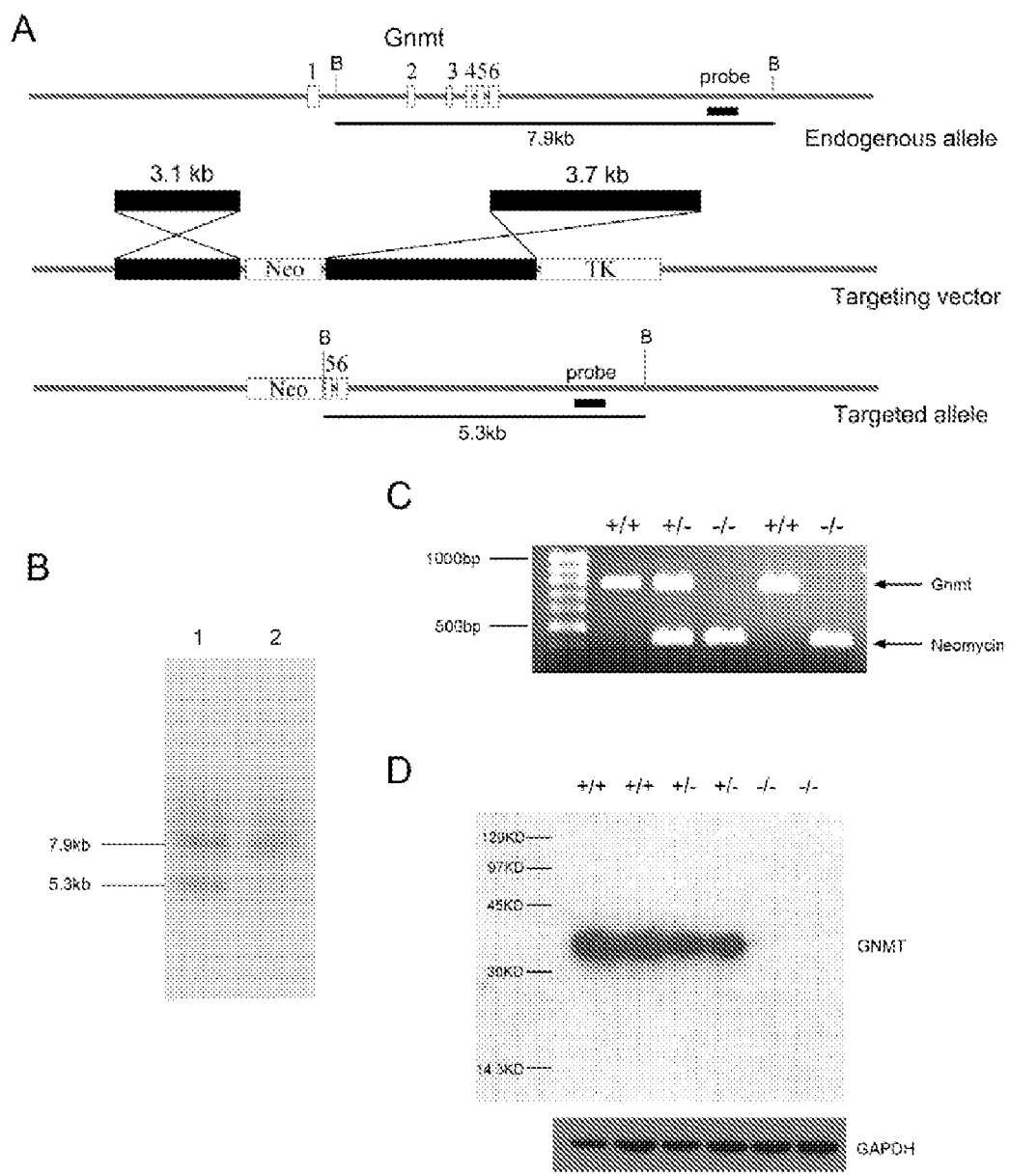
FIG. 2 shows targeted modification of the Gnmt gene locus. (A) Targeting vector was designed to replace Gnmt exons 1-4 and a part of exon 5 with a neomycin resistance gene. Neomycin positive selection marker is flanked by two homologous regions and followed by a TK negative selection marker at the 3' end of the targeting vector. (B) Southern blot analysis of embryonic stem cell clones. BamHI (B)-BamHI DNA fragment size decreased from 7.9 kb (wild-type allele) to 5.3 kb (recombinant allele). (C) Genotyping of Gnmt knockout mice by PCR. The normal Gnmt allele yielded a 772 bp fragment and the disrupted allele a 409 bp fragment. +/+, wild-type; +/−, Gnmt heterozygous and −/−, Gnmt−/− mice (D) Expression of GNMT protein confirmed by western blot analysis. Each lane contains 10 μg hepatic lysate. GNMT molecular mass: 32 kDa. GAPDH: internal control.
Figure 3:
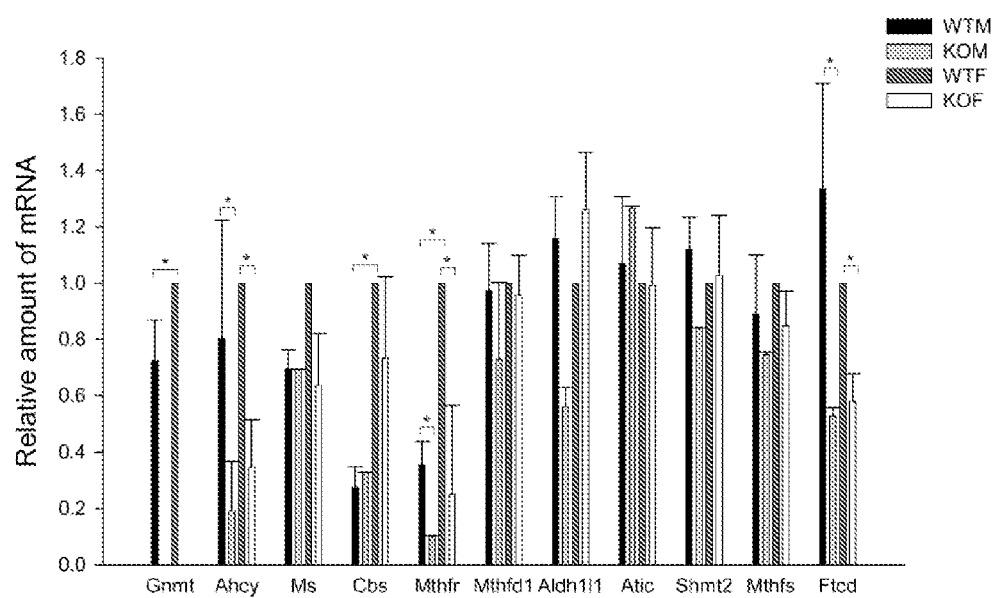
FIG. 3 shows the Real-time PCR analyses of mRNA expression levels of the genes involved in one-carbon metabolism pathway. The expression profiles of mRNA in WTM (wild-type male), KOM (Gnmt−/− male) and KOF (Gnmt−/− female) liver tissue were normalized to the WTF (wild-type female) mice. *, p<0.05. Ahcy, S-adenosylhomocysteine hydrolase; Ms, methionine synthase; Cbs, cystathionine beta-synthase; Mthfr, 5,10-methylenetetrahydrofolate reductase; Mthfd1, methylenetetrahydrofolate dehydrogenase (NADP+ dependent); methenyltetrahydrofolate cyclohydrolase; formyltetrahydrofolate synthase; Aldh1l1, aldehyde dehydrogenase 1 family; member L1; Atic, 5-aminoimidazole-4-carboxamide ribonucleotide formyltransferase/IMP cyclohydrolase; Shmt2, serine hydroxymethyl transferase 2; Mthfs, 5,10-methenyltetrahydrofolate synthetase; Ftcd, formiminotransferase cyclodeaminase.
Figure 4:
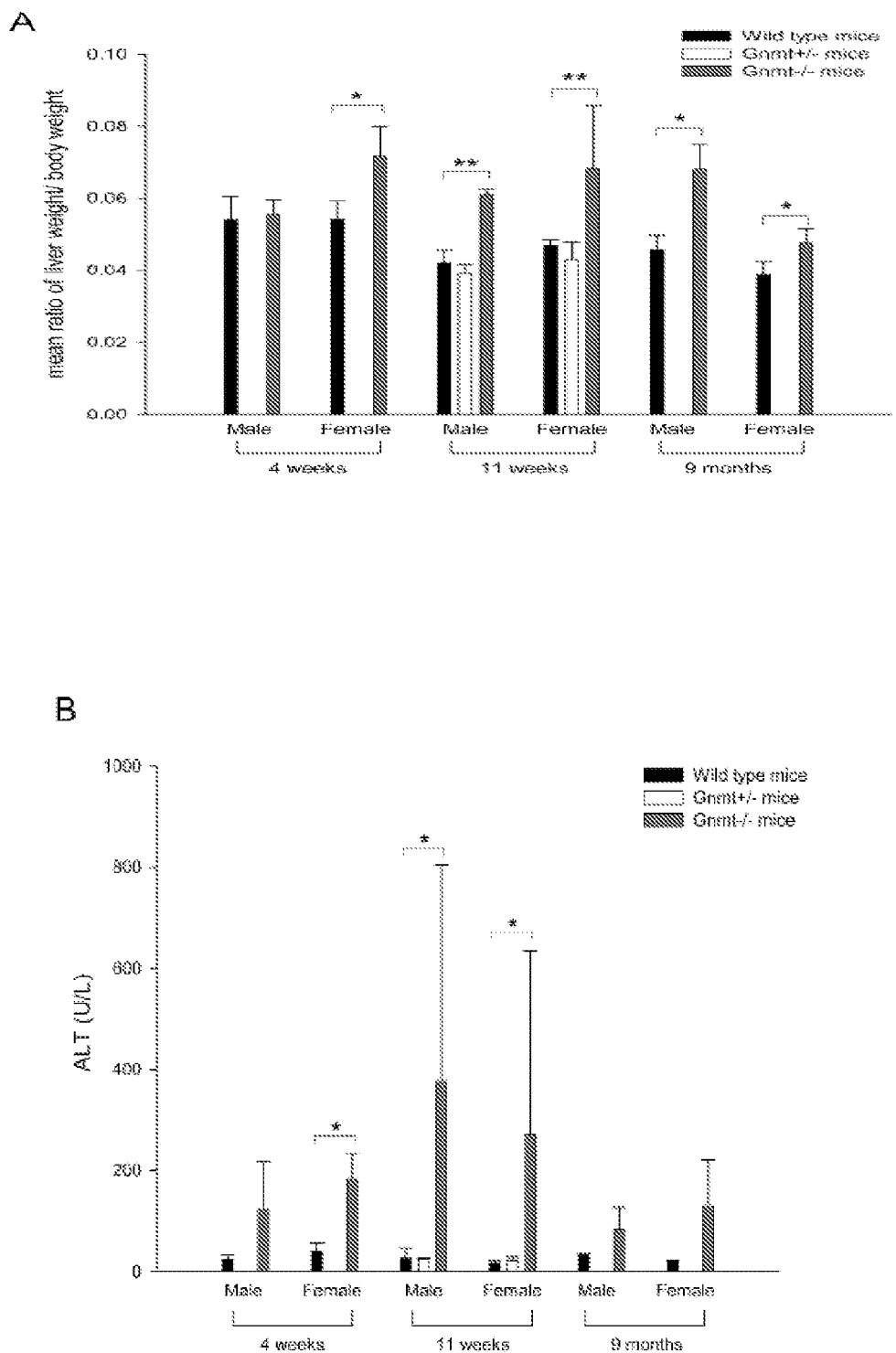
FIG. 4 depicts that gGnmt−/− mice had hepatomegaly and significantly higher levels of serum ALT. (A) Ratio of liver weight to body weight. (B) Comparison of serum ALT levels between wild-type, Gnmt+/−, and Gnmt−/− mice. *, p<0.05; **, p<0.01, both compared to wild-type mice.
Figure 5:
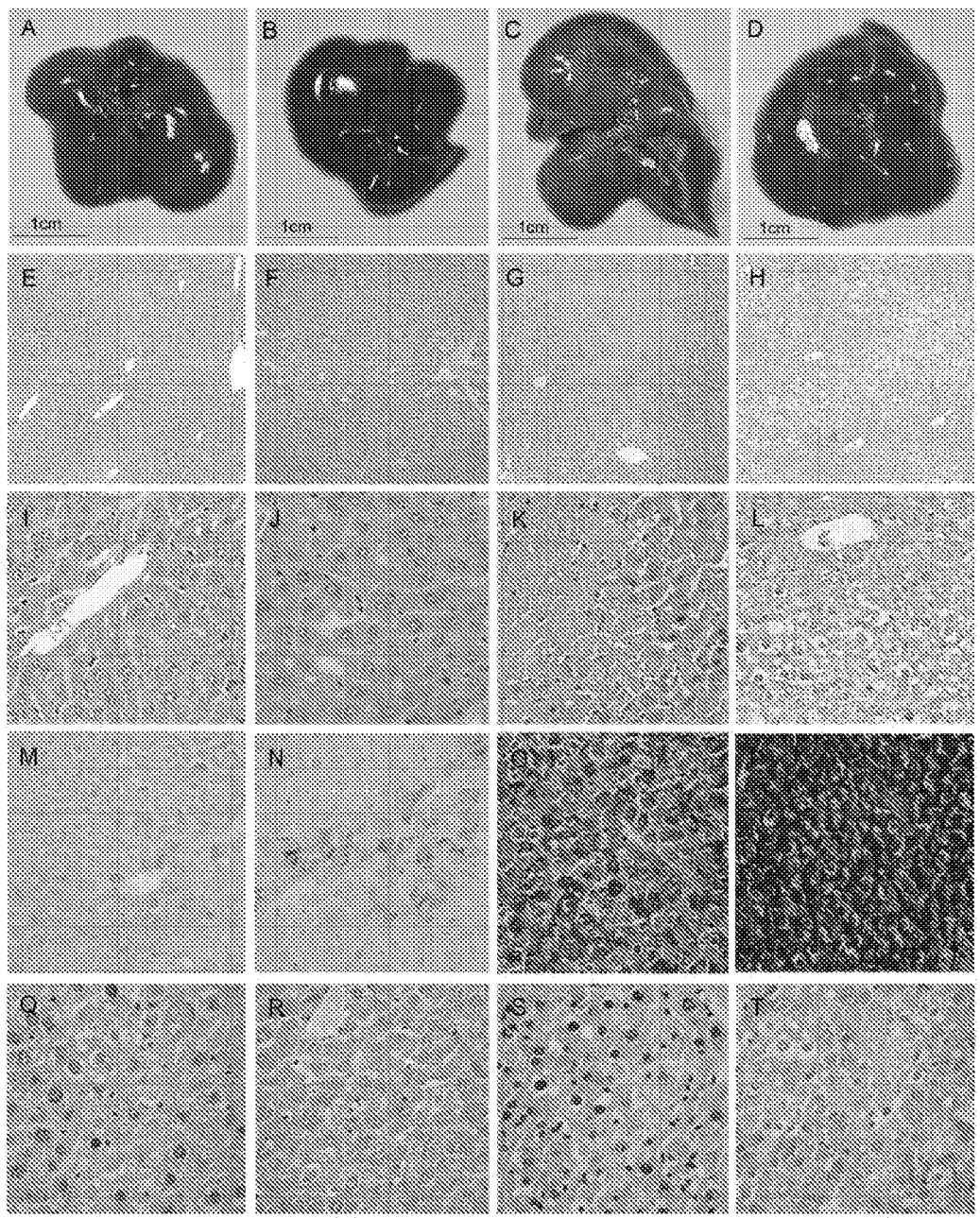
FIG. 5 shows the pathological examination of wild-type and Gnmt−/− mouse livers. Gross pathology of liver organs from male wild-type (A), male Gnmt+/− (B), male Gnmt−/− (C), and female Gnmt−/− mice (D). All the mice had been fasting for eight hours before they were sacrificed. HE staining of liver tissue from 11-week-old male wild-type (E and I), male Gnmt+/− (F and J), male Gnmt−/− (G and K), female Gnmt−/− (H and L), 9-month-old male Gnmt−/− (Q), and 9-month-old female Gnmt−/− mice (S). PAS staining of liver tissue from 11-week-old male wild-type (M), female wild-type (N), male Gnmt−/− (O), female Gnmt null (P), 9-month-old male Gnmt−/− (R), and 9-month-old female Gnmt−/− mice (T). Magnification: 100× for E-H, 400× for I-T.
Figure 6:
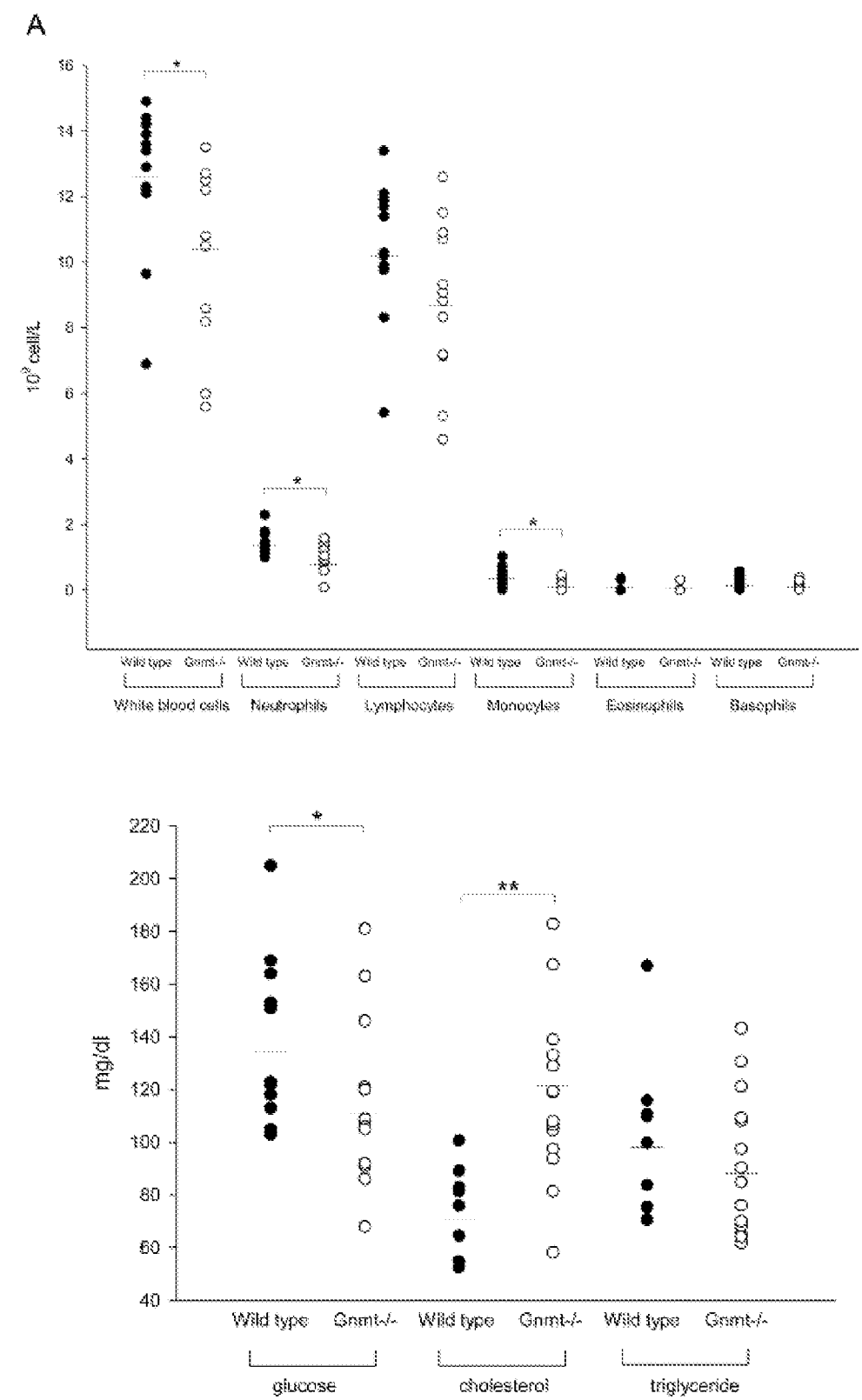
FIG. 6 shows Hematology and analysis of blood biochemical parameters of wild-type and Gnmt−/− mice. (A) White blood cell, neutrophil, lymphocyte, monocyte, eosinophil and basophil counts in wild type mice (solid circles) and Gnmt−/− mice (open circles). Horizontal bars indicate the mean counts. (B) Serum glucose, cholesterol, and triglyceride levels of wild type (solid circles) and Gnmt−/− mice (open circles). Horizontal bars indicate the mean serum concentration. *, p<0.05; **, p<0.01, both compared to wild-type mice.
Figure 7:
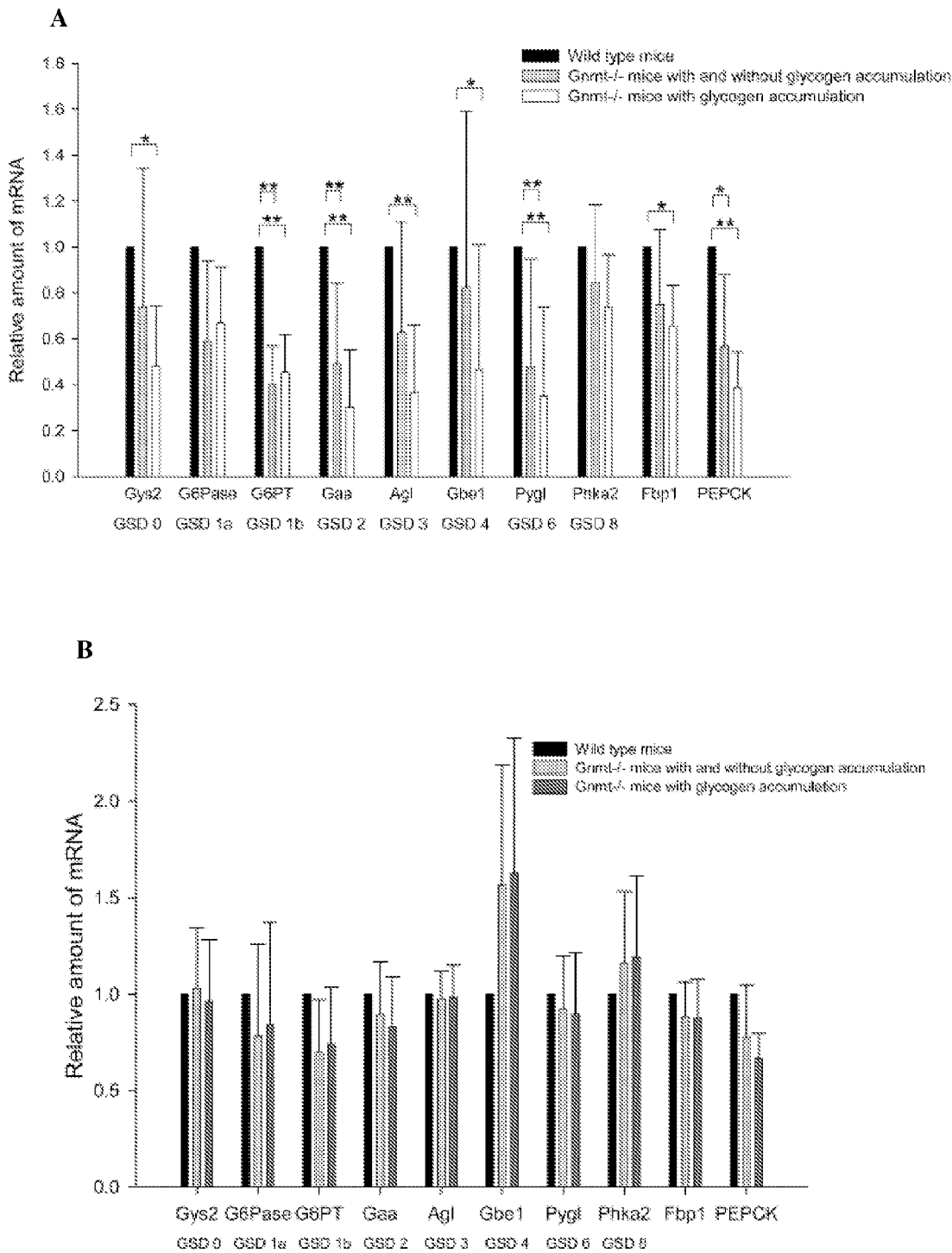
FIG. 7 shows Real-time PCR analysis of mRNA expression levels of genes linked with various types of GSD. The expression profiles of mRNA were normalized to the wild type mice. (A) The mice at 11 weeks of age; (B) The mice at 9 months of age. *, p<0.05; **, p<0.01. Gys2, glycogen synthase 2; G6Pase, glucose-6-phosphatase; G6PT, glucose-6-phosphate transporter; Gaa, alpha-glucosidase; Agl, amylo-1,6-glucosidase; Gbe1, branching enzyme 1; Pygl, glycogen phosphorylase; Phka2, phosphorylase kinase alpha 2; Fbp1, fructose 1,6-bisphosphatase; and PEPCK, phosphoenolpyruvate carboxykinase.
Figure 8:
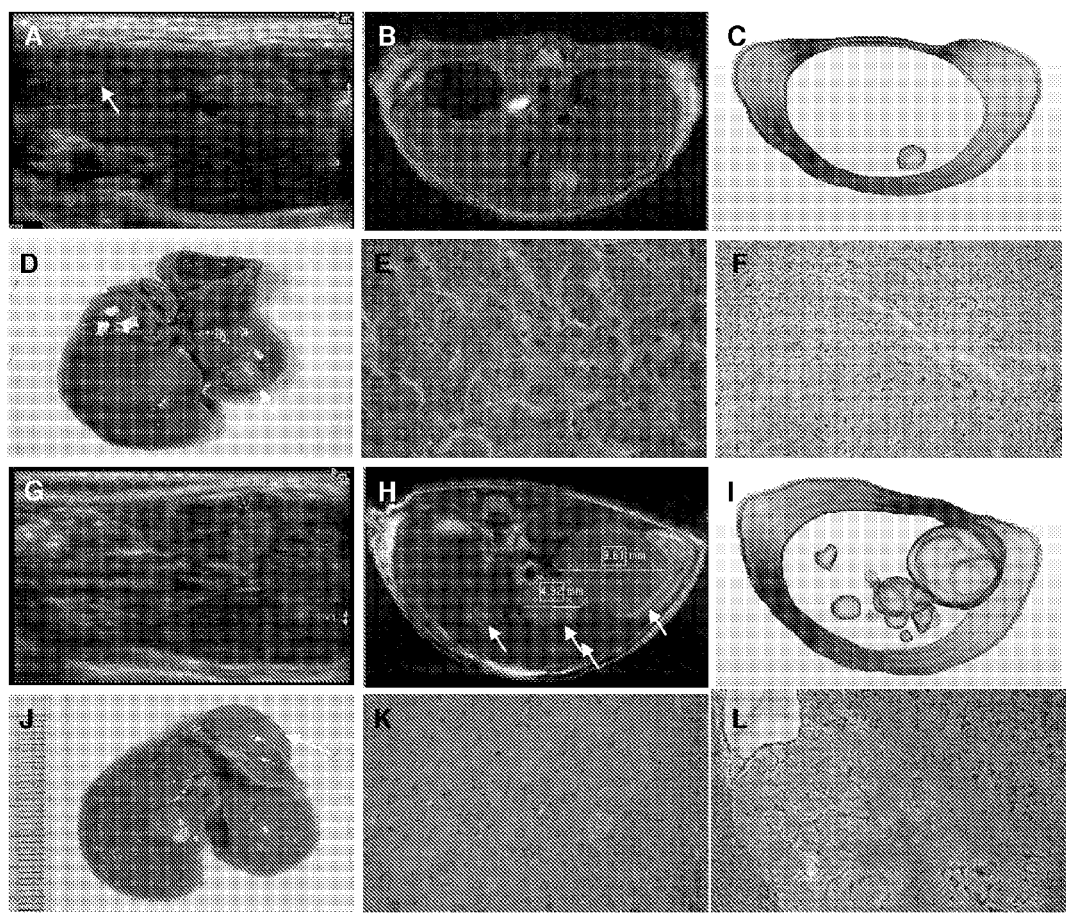
FIG. 8 is the result of ultrasound, MRI, gross pathology, HE stain and reticulin stain of male and male Gnmt−/− mice. Ultrasound of liver organs from male Gnmt−/− (A), female Gnmt−/− (G). MRI and MRI reconstruction of liver organs from male Gnmt−/− (B and C), and female Gnmt−/− mice (H and I). Gross pathology of liver organs from male Gnmt−/− (D), and female Gnmt−/− mice (J). HE staining of liver tissue from male male Gnmt−/− (E), and female Gnmt−/− (K). Reticulin staining of liver tissue from male male Gnmt−/− (F), and female Gnmt−/− (1).

The neomycin gene (to replace exons 1-4 and part of exon 5 of the mouse Gnmt gene) was framed with two DNA fragments (3.1 kb and 3.7 kb) in the targeting vector. The thymidine kinase gene was used as a negative selection marker (FIG. 2A). The 40 μg targeting vector was linearized using AscI and introduced into embryonic stem cells (129/Sv-derived) by electroporation. After screening 278 clones using southern blot analysis (FIG. 2B), a recombinant clone was isolated and used for microinjection into blastocytes. Four male chimeric mice were obtained and used to breed female C57BL/6 mice. Agouti $F_1$ offspring were subjected to PCR to detect the germline transmission of the disrupted allele. Heterozygous $F_1$ male mice were backcross with female wild-type C57B/6 mice to generate C57BL/6 genome background mice. PCR was developed to differentiate wild-type (+/+), Gnmt heterozygous (+/−), and Gnmt−/− mice. The primers used for PCR were shown as the following: GNMT-F (5'-GCGGCGGCCGCATGCTGGTGGAAGAGGGC) (SEQ ID NO: 1) and GNMT-R (5'-TTGCAGTCTGGCAAGTGAGC) (SEQ ID NO: 2) for GNMT; neomycin-F (5'-GTTCCT-TGCGCAGCTGTGCT) (SEQ ID NO: 3) and neomycin-R (5'-CGGCCACAGTCGATGAATCC) (SEQ ID NO: 4) for neomycin. The normal Gnmt allele yielded a 772bp fragment by Gnmt primers and the disrupted allele yielded a 409bp fragment by neomycin primers (FIG. 2C). The expression of GNMT protein in liver was analyzed using western blot; the results show that compared to the wild-type, GNMT expression decreased approximately 50% in the livers of Gnmt+/− mice and GNMT was undetectable in the livers of Gnmt−/− mice (FIG. 2D).

At 11 weeks of age, male and female wild-type, Gnmt+/− and Gnmt−/− mice (≧6 mice per group) were sacrificed for phenotypic analysis. SAM and SAH concentrations were detected by using HPLC. Compared to wild-type mice of the same gender, hepatic concentrations of SAM in Gnmt−/− mice significantly increased in both male and female mice (<0.05). In contrast, the hepatic concentration of SAM in Gnmt+/− mice was 2.8 fold lower than in wild-type mice (Table 1), and hepatic concentrations of SAH in male and female Gnmt−/− mice were similar to those in the wild-type mice. Accordingly, the SAM/SAH ratio increased 42- and 67-fold in the male and female Gnmt−/− mice, respectively (Table 1). Homocysteine levels remained unchanged across the different mouse groups. Methionine levels in the Gnmt−/− mice were 1.9 to 2.4-fold greater than in the wild-type mice (Table 1).

TABLE 1

Concentrations of hepatic SAM and SAH and levels of serum homocysteine and methionine from wild-type and Gnmt KO mice.

| | | SAM (nmol/g liver) | SAH (nmol/g liver) | SAM/SAH | Total Homocysteine (μM) | Methionine (mg/dl) |
|---|---|---|---|---|---|---|
| Wild-type | Male | 45.0 ± 23.4 | 71.9 ± 26.2 | 0.63 | 5.7 ± 0.03 | 0.74 ± 0.03 |
| | Female | 52.4 ± 29.3 | 64.2 ± 16.8 | 0.82 | 5.7 ± 0.04 | 0.74 ± 0.01 |
| | Total | 48.0 ± 24.6 | 68.8 ± 22.2 | 0.69 | 5.6 ± 0.13 | 0.75 ± 0.02 |
| Gnmt+/− | Male | 18.0 ± 4.6 | 77.1 ± 8.9 | 0.23 | 5.9 ± 0.10 | ND |
| | Female | 16.2 ± 10.2 | 70.4 ± 11.9 | 0.23 | 5.9 ± 0.20 | ND |
| | Total | 17.1 ± 7.1 | 73.7 ± 10.1 | 0.23 | 5.9 ± 0.17 | ND |
| Gnmt−/− | Male | 3085.4 ± 1276.9 | 73.3 ± 33.6 | 42.09 | 5.8 ± 0.10 | 2.04 ± 0.64 |
| | Female | 3882.0 ± 1978.8 | 57.7 ± 6.2 | 67.28 | 5.8 ± 0.30 | 2.47 ± 0.89 |
| | Total | 3453.1 ± 1617.9 | 66.5 ± 25.4 | 51.93 | 5.8 ± 0.19 | 2.23 ± 0.76 |

The phenotypes of Gnmt−/− mice have been followed up biweekly using magnetic resonance imaging (MRI) and ultrasound since they were 13 months of age. Among 6 GNMT−/− mice sacrificed, 1 male and 1 female mice had an early HCC nodule and at age of 18 and 14 months, 1 female mouse had an early HCC nodule and liver fatty nodules at age of 14 months, 1 female and 1 male mice had dysplastic nodules with markedly fatty changes in liver, and 1 male mouse had liver necrosis at age of 14 months (Table 2).

TABLE 2

The liver tumor formation of the Gnmt−/− mice at the age of 13-21 months

| | Gender | Age (m) | liver/body weight | No. of nodules | nodules >0.5 cm | nodules <0.5 cm | Pathology data |
|---|---|---|---|---|---|---|---|
| GNMT−/− | M | 13 | 7.23% | 0 | 0 | 0 | Fatty change, Necrosis |
| | M | 13 | 7.58% | 0 | 0 | 0 | Necrosis |
| | M | 18 | 9.48% | 1 | 1 | 0 | Dysplastic nodules, Early HCC |
| GNMT−/− | F | 14 | 10.62% | 7 | 3 | 4 | Fatty change, dysplastic nodule, Early HCC |
| | F | 15 | 6.23% | 2 | 0 | 2 | Fatty change |
| | F | 21 | 5.94% | 2 | 2 | 0 | Fatty change, Carvernous hemangioma |

Microarray analysis was applied to observe the difference metabolism between GNMT knockout and wild-type mice. Significantly increase of mRNA levels in both female (GNMT KO compared to wild type) and male (GNMT KO compared to wild type) mice were shown for 1896 and 2429 genes, respectively. Among these genes, 543 and 843 genes with more than twofold changes were selected to further functional analysis. We used CrossPath program to classify these genes by their functions based on KEGG pathway databases. Tables 3 and 4 showed the functional pathways in which increase two or more differentially expressed genes have been categorized in the given pathways. The major pathways increase in female and male GNMT KO mice are PPAR signaling pathway and cell cycle. In addition, cytokine-cytokine receptor interaction and MAPK signaling pathway were decreased in female and male GNMT KO mice. Table 5 shown the ratio of mRNA expression levels of genes belonging to different pathways in various tissues from Gnmt−/− mice vs. that expressed in liver tissues from age-mached wild type mice measured using real-time PCR. The results shown several survival and proliferation genes were significantly down-regulated in Gnmt−/− mice and three oncogenes were up-regulated in Gnmt−/− mice.

TABLE 3-1

Functional classification of regulatory genes in female and male GNMT KO mice at 11 weeks of ages by KEGG pathway database.

| Pathways that up-regulated in female GNMT−/− mice | No.* | Pathways that up-regulated in male GNMT−/− mice | No.* |
|---|---|---|---|
| PPAR signaling pathway | 17 | Cell cycle | 16 |
| Biosynthesis of steroids | 11 | Gap junction | 13 |
| MAPK signaling pathway | 10 | PPAR signaling pathway | 12 |
| Glutathione metabolism | 9 | Pyrimidine metabolism | 12 |
| Pyruvate metabolism | 7 | Purine metabolism | 11 |
| Xenobiotics by cytochrome P450 | 7 | Focal adhesion | 10 |
| Adipocytokine signaling pathway | 7 | Oxidative phosphorylation | 9 |
| Insulin signaling pathway | 6 | Tight junction | 8 |
| Jak-STAT signaling pathway | 6 | Glutathione metabolism | 7 |
| Colorectal cancer | 6 | Cytokine-cytokine receptor interaction | 7 |

| Pathways that down-regulated in female GNMT−/− mice | No.* | Pathways that down-regulated in male GNMT−/− mice | No.* |
|---|---|---|---|
| Cytokine-cytokine receptor interaction | 21 | MAPK signaling pathway | 24 |
| Cell adhesion molecules | 17 | Cytokine-cytokine receptor interaction | 16 |
| Focal adhesion | 16 | Focal adhesion | 15 |
| MAPK signaling pathway | 15 | Regulation of actin cytoskeleton | 13 |
| Regulation of actin cytoskeleton | 15 | Complement and coagulation cascades | 12 |
| Neuroactivate ligand-receptor interaction | 12 | Wnt signaling pathway | 12 |
| Calcium signaling pathway | 11 | Xenobiotics by cytochrome P450 | 12 |
| Wnt signaling pathway | 11 | Insulin signaling pathway | 12 |
| Hematopoietic cell lineage | 11 | Calcium signaling pathway | 12 |
| Insulin signaling pathway | 10 | Linoleic acid metabolism | 11 |
| Jak-STAT signaling pathway | 10 | Arachidonic acid metabolism | 10 |

*Number of genes that exhibited at least twofold expression difference between GNMT KO and wild type mice

TABLE 3-2

Functional classification of regulatory genes in female and male Gnmt−/− mice tumorous and tumor adjacent tissues at 14-18 months of ages by KEGG pathway database

| Pathways that up-regulated in female GNMT−/− mice | No.* | Pathways that up-regulated in male GNMT−/− mice | No.* |
| --- | --- | --- | --- |
| PPAR signaling pathway | 17 | Cell cycle | 16 |
| Biosynthesis of steroids | 11 | Gap junction | 13 |
| MAPK signaling pathway | 10 | PPAR signaling pathway | 12 |
| Glutathione metabolism | 9 | Pyrimidine metabolism | 12 |
| Pyruvate metabolism | 7 | Purine metabolism | 11 |
| Xenobiotics bycytochrome P450 | 7 | Focal adhesion | 10 |
| Adipocytokine signaling pathway | 7 | Oxidative phosphorylation | 9 |
| Insulin signaling pathway | 6 | Tight junction | 8 |
| Jak-STAT signaling pathway | 6 | Glutathione metabolism | 7 |
| Colorectal cancer | 6 | Cytokine-cytokine receptor interaction | 7 |

| Pathways that down-regulated in female GNMT−/− mice | No.* | Pathways that down-regulated in female GNMT−/− mice | No.* |
| --- | --- | --- | --- |
| Cytokine-cytokine receptor interaction | 21 | MAPK signaling pathway | 24 |
| Cell adhesion molecules | 17 | Cytokine-cytokine receptor interaction | 16 |
| Focal adhesion | 16 | Focal adhesion | 15 |
| MAPK signaling pathway | 15 | Regulation of actin cytoskeleton | 13 |
| Regulation of actin cytoskeleton | 15 | Complement and coagulation cascades | 12 |
| Neuroactivate ligand-receptor interaction | 12 | | |
| Calcium signaling pathway | 11 | Wnt signaling pathway | 12 |
| Wnt signaling pathway | 11 | Xenobiotics by cytochrome P450 | 12 |
| Hematopoietic cell lineage | 11 | Insulin signaling pathway | 12 |
| Insulin signaling pathway | 10 | Calcium signaling pathway | 12 |
| Jak-STAT signaling pathway | 10 | Linoleic acid metabolism | 11 |
| | | Arachidonic acid metabolism | 10 |

*Number of genes that exhibited at least twofold expression difference between tumorous and tumor adjacent tissues from Gnmt−/− mice

TABLE 4

Functional classification of down-regulatory genes in female and male GNMT KO mice by KEGG pathway database.

| Pathways that down-regulated in female GNMT−/− mice | No.* | Pathways that down-regulated in male GNMT−/− mice | No.* |
| --- | --- | --- | --- |
| Cytokine-cytokine receptor interaction | 21 | MAPK signaling pathway | 24 |
| Cell adhesion molecules | 17 | Cytokine-cytokine receptor interaction | 16 |
| Focal adhesion | 16 | Focal adhesion | 15 |
| MAPK signaling pathway | 15 | Regulation of actin cytoskeleton | 13 |
| Regulation of actin cytoskeleton | 15 | Complement and coagulation cascades | 12 |
| Neuroactivate ligand-receptor interaction | 12 | Wnt signaling pathway | 12 |
| Calcium signaling pathway | 11 | Xenobiotics by cytochrome P450 | 12 |
| Wnt signaling pathway | 11 | Insulin signaling pathway | 12 |
| Hematopoietic cell lineage | 11 | Calcium signaling pathway | 12 |
| Insulin signaling pathway | 10 | Linoleic acid metabolism | 11 |
| Jak-STAT signaling pathway | 10 | Arachidonic acid metabolism | 10 |

*Number of genes that exhibited at least twofold expression difference between GNMT KO and wild type mice

TABLE 5

The ratio of mRNA expression levels of genes belonging to different pathways in various tissues from Gnmt−/− mice vs. that expressed in liver tissues from age-mached wild type mice measured using real-time PCR.

| | 11-w Gnmt−/− mice | | 18-m Gnmt−/− | | 14-m Gnmt−/− | |
| --- | --- | --- | --- | --- | --- | --- |
| | Male | Female | Male | | Female | |
| Gene category | KO/WT$^a$ | KO/WT$^a$ | TA/WT$^b$ | T/WT$^c$ | TA/WT$^b$ | T/WT$^c$ |
| Survival and proliferation | | | | | | |
| PTEN | 1.32 | 1.07 | 0.60 | 0.37 | 0.56 | 0.08 |
| PI3K | 0.60 | 0.47 | 0.26 | 0.36 | 0.40 | 0.69 |
| Akt 1 | 1.40 | 1.28 | 0.95 | 0.74 | 0.64 | 0.48 |

TABLE 5-continued

The ratio of mRNA expression levels of genes belonging to different pathways in various tissues from Gnmt−/− mice vs. that expressed in liver tissues from age-mached wild type mice measured using real-time PCR.

|  | 11-w Gnmt−/− mice | | 18-m Gnmt−/− | | 14-m Gnmt−/− | |
|---|---|---|---|---|---|---|
|  | Male | Female | Male | | Female | |
| Gene category | KO/WT[a] | KO/WT[a] | TA/WT[b] | T/WT[c] | TA/WT[b] | T/WT[c] |
| GSK3β | 1.20 | 0.71 | 0.75 | 1.14 | 1.20 | 0.70 |
| β-catenin | 1.58 | 1.07 | 0.65 | 0.65 | 0.78 | 0.47 |
| Oncogenes | | | | | | |
| Cyclin D1 | 6.55 | 5.57 | 3.35 | 2.41 | 1.73 | 1.50 |
| C-myc | 1.97 | 1.56 | 1.88 | 1.42 | 0.78 | 0.65 |
| C-Jun | 2.55 | 2.47 | 2.54 | 3.97 | 1.41 | 1.47 |
| Tumor suppressor gene | | | | | | |
| Rb | 3.20 | 0.75 | 0.64 | 1.00 | 1.57 | 0.73 |
| p53 | 1.96 | 1.16 | 1.40 | 1.62 | 1.07 | 0.83 |

PTEN, phosphatase and tensinhomolog;
PI3K, phosphatidylinositol 3-kinase;
GSK3β, glycogen synthase kinase;
Rb, retinoblastoma;
T, tumorous tissues;
TA, tumor adjacent tissues;
KO, Gnmt−/− mice;
WT, wild-type mice
[a]ratio of the gene expression profiles between Gnmt−/− and wild-type mice at the 11 weeks of age. The raw data was normalized to GAPD internal control.
[b]ratio of the gene expression profiles between tumor adjacent tissues and wild-type mice liver tissues. The raw data was normalized to GAPD internal control.
[c]ratio of the gene expression profiles between tumorous tissues and wild-type mice liver tissues. The raw data was normalized to GAPD internal control.

To demonstrate that the Gnmt−/− mouse model is more susceptible to carcinogens, aflatoxin B1 (AFB1) was used to challenge the mice. The AFB1 was administrated intra-peritoneally twice with the following dosages: 10 ug per body weight in gram on the $7^{th}$ day of age and 40 ug at the $9^{th}$ weeks of age. The results showed that liver nodules were detected in all (5/5) female and 57.1% (4/7) male Gnmt−/− mice treated with AFB1, while neither the wild-type mice treated with AFB1 nor the other groups of mice treated with solvent (tricaprylin) have developed liver tumors at the age of 13-14 months old (Table 6)

EXAMPLE 2

Materials and Methods:

Cell Culture and Treatment.

Hepatocellular carcinoma cell line [HA22T/VGH] was prepared according to Waxman, D. J. & O'Connor, C. Growth Hormone Regulation of Sex-Dependent Liver Gene Expression. *Molecular Endocrinology* 20, 2613 (2006), and the

TABLE 6

The liver tumor formation of the 2 genotypes mice treated with solvent or AFB1 at the age of 13 months old.

| | | Gender | No. | No. mice with nodules | Nodules >0.5 cm | <0.5 cm | No. mice with nodules >0.5 cm | ALT (U/L) | AST (U/L) |
|---|---|---|---|---|---|---|---|---|---|
| AFB1 | wild type | M | 8 | 0/8 (0%) | 0 | 0 | 0/8 (0%) | 27.5 ± 0.71 | 72.00 ± 58.92 |
| | | F | 8 | 0/8 (0%) | 0 | 0 | 0/8 (0%) | 22.83 ± 3.92 | 42.50 ± 8.22 |
| | Gnmt−/− | M | 7 | 4/7 (57.1%) | 5 | 6 | 3/7 (43.9%) | 89.67 ± 63.13 | 106.00 ± 54.21 |
| | | F | 5 | 5/5 (100%) | 4 | 3 | 4/5 (80%) | 182.33 ± 95.26 | 266.33 ± 249.52 |
| Solvent | wild type | M | 6 | 0/6 (0%) | 0 | 0 | 0/6 (0%) | 20.00 ± 0.00 | 74.00 ± 21.21 |
| | | F | 8 | 0/8 (0%) | 0 | 0 | 0/8 (0%) | 20.17 ± 4.45 | 47.67 ± 6.56 |
| | Gnmt−/− | M | 4 | 0/4 (0%) | 0 | 0 | 0/4 (0%) | 124.00 ± 127.28 | 155.50 ± 144.96 |
| | | F | 4 | 0/4 (0%) | 0 | 0 | 0/4 (0%) | 76.00 ± 26.92 | 98.50 ± 18.43 |

Figure 9:
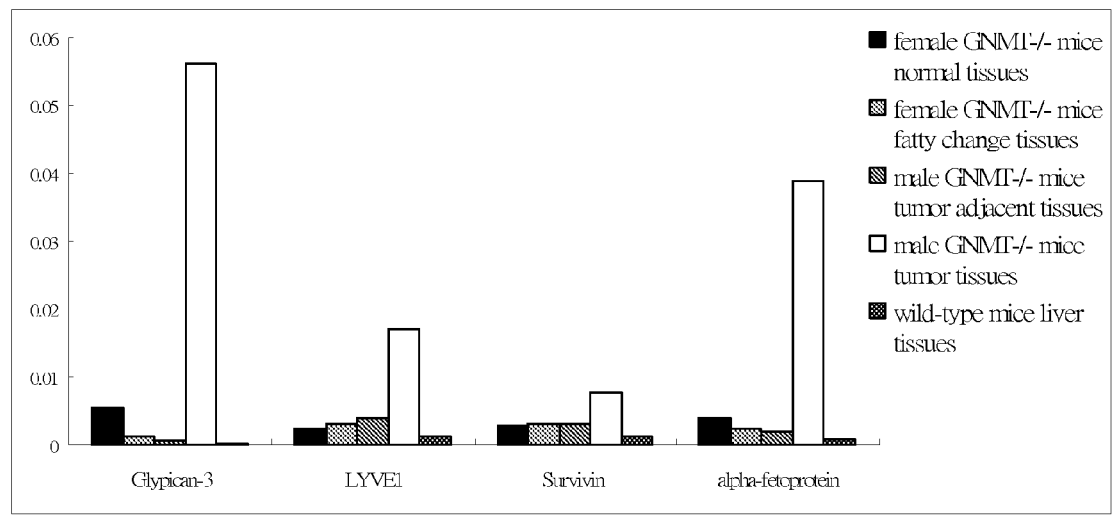
FIG. 9 shows Real-time PCR analysis of several early HCC markers (glypican-3, LYVE1, survivin and alpha-fetoprotein) in the wild-type and Gnmt−/− mice.

HE staining of histological mouse liver sections revealed no abnormalities in the wild-type mice treated with AFB1. However, we observed Dysplastic nodule, early HCC and fatty nodules in the male Gnmt−/− mice treated with AFB1 (FIG. 9). Sclenosing HCC, Dysplastic nodule with focal fatty change were observed in the female Gnmt−/− mice (FIG. 9).

stable expression clones from human hepatoblastoma cell line-HepG2 was prepared based on Mode, A. & Gustafsson, J. A. Sex and the Liver—A Journey Through Five Decades. *Drug Metabolism Reviews* 38, 197-207 (2006), [SCG2] as stated in the paper Chen, S. Y et al. Glycine N-methyltransferase tumor susceptibility gene in the benzo(a)pyrene-detoxification pathway. *Cancer Res.* 64, 3617-3623 (2004). were used in this example. Cells were maintained in Dulbecco's Modified Eagle Medium (DMEM) (GIBCO BRL, Grand Island, N.Y.) containing 10% fetal bovine serum (Hyclone). $AFB_1$ was solved in DMSO and treatment was performed in culture medium.

Immunofluorescent Staining and Confocal Microscopy.

Cultured HA22T/VGH cells were placed on coverslips and treated with 20 µM $AFB_1$ or 0.1% DMSO for 3 hr, fixed with 4% paraformaldehyde in PBS pH 7.4 (solution I) at room-temperature for 20 min. After the cells were incubated in permeablization solution (fixing solution I plus 0.5% Triton X-100) at room temperature for 5 min, the coverslips were incubated with blocking buffer (5% BSA in PBS) at room temperature for 1 hr and then with rabbit anti-GNMT antiserum (1:200) for another 1 hr. The FITC-conjugated goat anti-rabbit IgG (Chemicon, Temecula, Calif., USA) were used as secondary antibodies. Nuclei were counterstained with Hoechst H33258 (Sigma-Aldrich). Confocal microscopy was performed using an Olympus IX70 inverted fluorescence microscope outfitted with the Olympus Fluoview Argon/Krypton scanning laser system and Fluoview image analysis software (Olympus, Melville, N.Y.).

LGA Dockings.

LGA was used to elucidate interaction sites between $AFB_1$ and various forms of GNMT. Autodock 3.0 software was used to identify the most favorable ligand binding interactions. As mentioned earlier, X-ray crystallography data from rat GNMT was used for docking purposes because it has a 91% amino acid sequence homology with human GNMT (Pakhomova, S. et al., *Proteins Structure Function and Bioinformatics* 57, 331-337, 2004). Parameters included 10 runs, a population size of 50, and a run termination criterion of 27,000 generations or $2.5 \times 10^5$ energy evaluations (whichever came first). A root mean square deviation conformational clustering tolerance of 0.5 Å was calculated from the ligand's crystallographic coordinates. Procedural details are available in previous report (Morris G M et al. *J Comput Chem* 19, 1639-1662, 1998).

Cytotoxicity Assay.

MTT assay was used to determine the cytotoxicity effect of $AFB_1$. In brief, cells were seeded on 96 well plate. At the time of assay, culture medium was replaced by 100 µL fresh medium containing 10 µL of 5 mg/mL MTT stock solution for each well. After 4 hr of labeling cells with MTT, medium was removed then 100 µL DMSO was added to each well for 10 min at 37° C. Samples were mixed and read absorbance at 540 nm. For half lethal concentration (LC50) determination, seven thousand HuH-7 cells were seeded on 96 well plate for 18 hr. Cells were treated with different concentration of $AFB_1$ and MTT assay was performed at series time points, triplicate for each set. The survival percentage is calculated by dividing the OD value of treatment group by solvent control group. For cytotoxicity assay, five thousand HuH-7 cells were infected with different amount of adenovirus or lentivirus carrying GNMT cDNA for 8 hr then refreshed medium for another 10 hr. After 72 hr of $AFB_1$ treatment, MTT assay was performed to determine the survival percentage.

Competitive ELISA for Quantifying $AFB_1$-DNA Adducts.

To evaluate the protective effect of GNMT, stable SCG2-1-1 cell clones or GNMT recombinant adenovirus (Ad-GNMT) infected HepG2 cells were cultured overnight in a 10-cm petri dish, treated with $AFB_1$ or 0.1% DMSO for 16 hrs, then harvested for DNA extraction. All samples were treated with 15 mM $Na_2CO_3$ and 30 mM $NaHCO_3$ (pH 9.6) at 37° C. for 2 hrs to ensure the neutralization of all adducts in ring-opened form. $AFB_1$-DNA adduct levels were measured with a competitive ELISA using 6A10 antibody, as previously described as Hsieh, L. L. et al., Immunological detection of aflatoxin B1-DNA adducts formed in vivo. *Cancer Res.* 48, 6328-6331 (1988). Each ELISA assay was performed in triplicate. Absorption levels were read at 490 nm.

The pPEPCKex-flGNMT Transgenic Construct.

We used a liver and kidney-specific transgenic vector, pPEPCKex, which contains the mouse phosphoenolpyruvate carboxykinase (PEPCK; Valera, A. et al., *Proc. Natl. Acad. Sci. U.S.A* 91, 9151-9154, 1994) promoter, a 0.3-kb synthetic intron and a 0.6-kb human growth hormone poly (A) signal. The pPEPCKex-flGNMT transgenic plasmid was constructed by placing the 1,2-kb human GNMT cDNA (from the 9-1-2 plasmid; Chen, Y. M. et al., *Int. J. Cancer* 75, 787-793, 1998) into the NotI and XhoI sites of the pPEPCKex vector. The pPEPCKex-flGNMT plasmid was digested with AscI and the linear 4,3-kb fragment was used for the microinjection.

Generation of GNMT TG Mice.

The GNMT TG mice were generated by pronucleus microinjection of FVB fertilized eggs. Mice were bred in a specific pathogen free facility. The tails of individual mice were cut on weaning at 3 weeks of age. Genomic DNA was isolated by proteinase K/SDS digestion (Promaga) and phenol/chloroform extraction method. The genotype of TG mice was determined by PCR. To detect the GNMT-TG, the 668-bp human GNMT specific DNA fragment was amplified by PCR with cycling conditions of 94° C. for 30 sec, 60° C. for 30 sec, 72° C. for 1 min for 30 cycles using primers GNMT-F 5'-GCGGCGGCCGCATGCTGGTGGAAGAGGGC-3' (SEQ ID NO: 1) and GNMT-R 5'- GCGCTCGAGTCAGTCTGTCCTCTTGAGCAC-3' (SEQ ID NO: 5).

$AFB_1$ Challenge.

$AFB_1$ (Sigma Co, St Louis, Mo.) was dissolved in tricaprylin (Sigma) at a concentration of 0.2 mg/mL. At 7 days of age, more than 6 mice in each group were injected with aflatoxin $B_1$ (10 mg $AFB_1$/kg of body weight) intraperitoneally, and boosted the same dose at 2 months. The protocol has been modified by Ghebranious and Sell previously (Ghebranious, N. & Sell, S. *Hepatology* 27, 383-391,1998). At 9 months after the injection, the mice were sacrificed for pathological examination. Two-fifth of the organs (including liver, lung and kidney) were fixed with 10% formalin for histopathological exam; the remaining parts of the organs were stored at −80° C. for in situ hybridization, DNA, RNA, and protein analyses.

RNA Analysis.

Total RNA was extracted from frozen tissue using TRIzol reagents (Invitrogen, Carlsbad, Calif.) according to the manufacturer's instructions. The amount for all RNA samples was quantified by spectrophotometer. Northern blot hybridization was performed as described previously. The cDNA probes generated from human GNMT gene of plasmid 9-1-2. Complementary DNA was produced from hepatic RNA (2 μg) using a SuperScript II RNase H-Reverse Transcriptase Kit (Invitrogen). The sequences of primers for GNMT were F1: GCGGCGGCCGCATGCTGGTGGAAGAGGGC (SEQ ID NO: 1) and R1: GCGCTCGAGTCAGTCTGTCCTCT-TGAGCAC (SEQ ID NO: 5); and for β-actin were F2: GTGGGGCGCCCCAGGCACCA (SEQ ID NO: 6) and R2: CTCCTTAATGTCACGCACGATTTC (SEQ ID NO: 7). The PCR conditions were as follows: pre-denaturation at 94° C. for 5 min followed by 30 cycles of amplification at 94° C. for 30 secs, 60° C. for 30 secs, and 72° C. for 1 min, followed by one 10 min extension at 72° C.

Western Blot Assay.

To perform western blot analysis, 10 μg of whole liver protein extract was separated by 10% SDS-PAGE and transferred to polyvinylidene difluoride membranes (PVDF; Amersham Pharmacia Biotech, Piscataway, N.J.). Procedures have been described in Waxman, D. J. & O'Connor, C. Growth Hormone Regulation of Sex-Dependent Liver Gene Expression. *Molecular Endocrinology* 20, 2613 (2006). In this test, mouse anti-GNMT monoclonal antibody (mAB) 14-1 was used to detect GNMT[20].

GNMT Enzyme Activity Assay.

This method is modified from procedures reported at Cook, R. J. & Wagner, C. Glycine N-methyltransferase is a folate binding protein of rat liver cytosol. *Proc. Natl. Acad. Sci. U.S. A* 81, 3631-3634 (1984). It was used to measure the GNMT enzyme activity of liver tissues from GNMT-TG mice. Portions of liver was homogenized with three volumes of ice-cold phosphate buffer (10 mM, pH 7.0) containing 0.25 M sucrose, 1 mM EDTA, 1 mM sodium azide, and 0.1 mM phenymethylsulfonylflouride. After centrifugation at 20,000×g for 30 min, the resulting supernatant was removed and 2-mercaptoethanol is added to a final concentration of 10 mM. The concentration of the protein was measured and 250 ug protein was added to a 100 ul reaction mixture containing of 100 mM Tris buffer (pH 7.4), 50 mM glycine, 0.23 mM SAM, and 2.16 uM S-adenosyl-$_L$-[methyl-$^3$H]-methionine (76.4 Ci/mmol). Following incubation at 37° C. for 30 min, reaction is terminated by the addition of a 50 ul mixture of 10% trichloroacetic acid and 5% activated charcoal. Each reaction is performed in triplicate.

Immunohistochemical Staining.

The immunohistochemical detection of the GNMT protein was performed using a monoclonal antibody (mAB) 14-1 at 1:200 dilution. The paraffin-embedded liver sections (4 um) were incubated with the GNMT antibody and detected with the DAB kit (DakoCytomation) according to the manufacturer's instructions.

EXAMPLE 3

GNMT Nuclear Translocation is Induced by $AFB_1$

Figure 10:
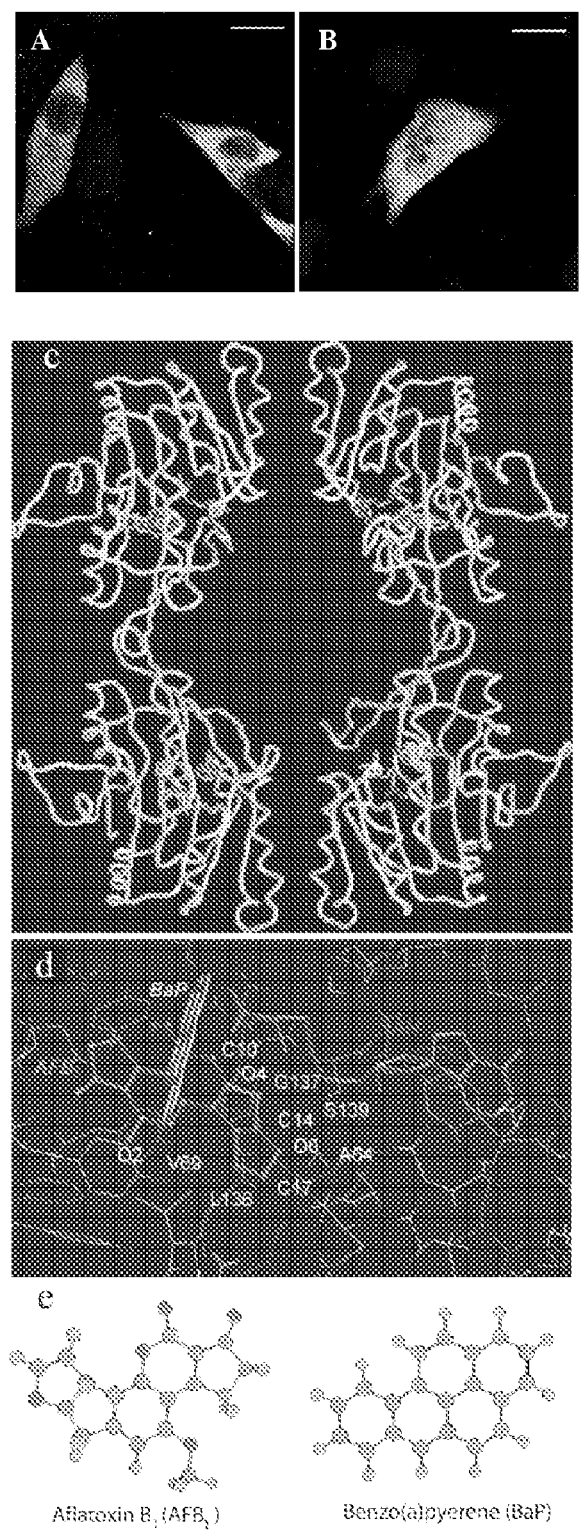
FIG. 10 shows (A-B) Nuclear translocation of glycine N-methyltransferase (GNMT) following treatment with aflatoxin B1. HA22T cells on coverslips were transfected with 5 g GNMT-Flag and treated with DMSO solvent (A) or 40 M AFB1 (B) prior to fixing and reaction with R4 (rabbit anti-GNMT) antisera. For immunofluorescent staining we used FITC-conjugated goat antirabbit antibodies. Nuclei were stained with Hoechst H33258. Bars: 20 M. (C-E) Model of benzo(a)pyrene (BaP) and aflatoxin B1 (AFB1) docking with the tetrameric form of GNMT using the Lamarckian genetic algorithm. (C) BaP (green) and AFB1 (red) molecules docked with the S-adenosylhomocystine-bound tetrameric form of rat GNMT (cyan) (PDB code 1D2H).(D) A monomer showing docked models of BaP (green) and AFB1 (red) molecules. GNMT amino acid residues (Ala64, Val69, Leu136, Gly137 and Ser139) in close proximity to several AFB1 carbon atoms are indicated according to the GNMT structure (PDB code 1D2H) and the docking model of the GNMT-AFB1 complex. (E) Structures of AFB1 (left) and BaP (right).

GNMT cDNA transfected HA22T/VGH cells (FIGS. 10A and B) with $AFB_1$ or DMSO (solvent control) for 16 hours. As shown in FIG. 10, GNMT distribution was initially restricted to the cytoplasm (FIG. 10A), but was partly translocated to cell nuclei following $AFB_1$ treatment (FIG. 10B). These results showed that $AFB_1$, as well as BaP, induces the nuclear translocation of GNMT.

It demonstrated that GNMT exhibited nuclear translocation in $AFB_1$ treated cells (FIG. 10). It also showed that GNMT can reduce the formation of $AFB_1$-DNA adducts and increase the survival rate of $AFB_1$-treated cells. $AFB_1$-DNA adducts formation have been implicated in liver carcinogenesis (Bressac, B. et al., *Nature* 350, 429-431, 1991; Hsu, I. C. et al., *Nature* 350, 427-428, 1991). It also proofed that the depletion of GNMT in hepatocyte raised the sensitivity of liver to this carcinogen. Given the choice, GNMT is involved in a cellular defense mechanism against these environmental carcinogens.

EXAMPLE 4

Modeling GNMT-$AFB_1$ Interaction

A combination of a Lamarckian genetic algorithm (LGA) and X-ray crystallography data was used to predict physical interactions between GNMT and $AFB_1$. Due to its 91% amino-acid sequence homology with the human GNMT protein, we relied on X-ray crystallography of the rat GNMT protein for our $AFB_1$ docking experiments. According to the data presented in Table 7, $AFB_1$ bound to both dimeric (Protein Data Bank code 1D2C) and tetrameric (1D2G) forms of GNMT at low binding energy levels (−9.41 and −10.06 kcal/mol, respectively).

TABLE 7

Lamarckian Genetic Algorithm Dockings Between GNMT Protein and $AFB_1$ Molecules[a]

| PDB Code[b] | Small Molecule | Cluster Number | Cluster Population | Mean Energy (kcal/mol) | Number of Evaluations | Protein Details |
| --- | --- | --- | --- | --- | --- | --- |
| 1D2C[c] | $AFB_1$ | 5 | 5 | −9.41 | $2.5 \times 10^5$ | GNMT dimmer |
| 1D2H[c] | $AFB_1$ | 2 | 9 | −9.83 | $2.5 \times 10^5$ | GNMT R175K mutant tetramer binding with SAM |
| 1XVA[d] | SAM | 2 | 5 | −9.85 | $2.5 \times 10^5$ | GNMT dimer without SAM |
| 1XVA[e] | $AFB_1$ | 4 | 4 | +53.25 | $2.5 \times 10^5$ | GNMT dimer binding with SAM |
| 1D2G[c] | $AFB_1$ | 1 | 10 | −10.06 | $2.5 \times 10^5$ | GNMT R175K mutant tetramer |

Results from a comparison of the binding energy of $AFB_1$ with GNMT dimer (1XVA) without SAM (−9.85 kcal/mol) and $AFB_1$ with GNMT dimer already bound with SAM (53.25 kcal/mol) suggest that $AFB_1$ competes with SAM to bind with GNMT. With slight differences in molecular orientation, the $AFB_1$ molecule, as well as BaP, is located at the same position inside the molecular basket in both the GNMT dimer and tetramer (FIG. 10C). GNMT amino acid residues in close proximity to $AFB_1$ (Ala64, Val69, Leu136, Gly137, and Ser139) are shown in FIG. 10D.

The example demonstrated (a) an $AFB_1$-binding domain at the substrate (SAM)-binding site of GNMT, and (b) that $AFB_1$ binds with both dimeric and tetrameric forms of GNMT. The R175K mutant form of the GNMT tetramer (1D2G) was used to demonstrate that R/K residue in close vicinity (~5 Å) of the binding site exerts practically zero effect on GNMT-$AFB_1$ cluster formation (Table 7). This result corresponds with the argument that GNMT is an example molecular basket. This unique structure feature might be consistent with the fact that GNMT can not only bind to SAM but also the polycyclic aromatic hydrocarbon (PAH) molecules such as benzo[a]pyrene. According to the crystal structure of GNMT, there are many tyrosine residues (33, 44, 177, 194, 220, 242, 283) located at the inner surface of the active site. This and other residues may provide an interacting environment to carcinogens. It is plausible that GNMT can also bind to $AFB_1$.

EXAMPLE 5

$AFB_1$-Induced Cytotoxicity Antagonized By GNMT

Figure 11:
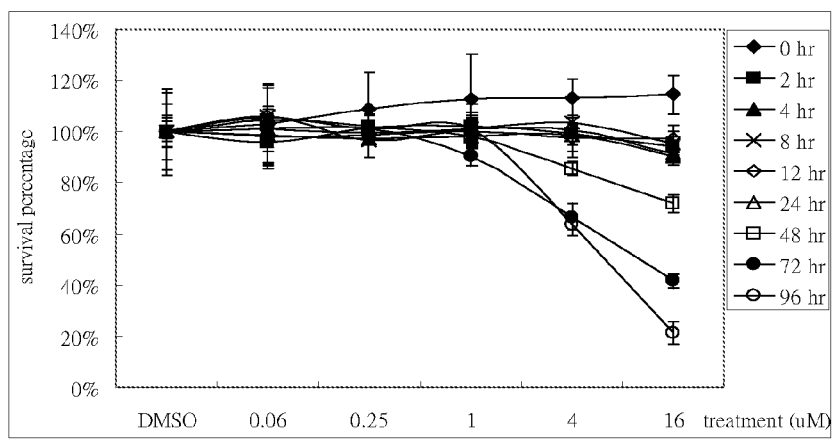
FIG. 11 shows GNMT antagonized the cytotoxicity effect of AFB1. (A-C) AFB1-induced cytotoxicity is reduced by GNMT overexpression. MTT assay was used to determine the survival percentage of HuH-7 cells treated with AFB1. A. Survival curve of HuH-7 cells treated with different amount of AFB1 at series time points. The 50% inhibitory concentration is dependent on the duration of treatment. The IC50 of AFB1 on HuH-7 cells be treated for 72 hr is about 12 M. B. HuH-7 cells were infected with Adenovirus carried GNMT gene or GFP control gene for 16 hr. After 72 hr of AFB1 treatment, cells were subjected to MTT assay. The survival rates of HuH-7 cells increased slightly by the dosage of Ad-GNMT. At the group of HuH-7 cells treated with 8 M AFB1, the survival rates of HuH-7 cells increased significantly by the dosage of Ad-GNMT. C. Similar results were observed in another system in which HuH-7 cells were transducted with the GNMT gene via a lentiviral vector. * p<0.05, ** p<0.01. (D-E) GNMT overexpression reduced the formation of AFB1-DNA adducts. D, SCG2-neg and SCG2-1-1 cells were treated with DMSO or indicated concentration AFB1 prior to harvesting for DNA extraction. AFB1-DNA adducts were measured with a competitive ELISA. White box and gray box indicate SCG2-neg and SCG2-1-1, respectively. Data represent the mean ±SD. *, p<0.01; **, p<0.001 by t-test. E, Ad-GFP- and Ad-GNMT-infected HepG2 cells were used to perform this assay. White box indicated Ad-GFP-infected HepG2 cells; gray box, 5 MOI Ad-GNMT infected HepG2 cells; black box, 50 MOI Ad-GNMT-infected HepG2 cells. *, by one way ANOVA.
Figure 11:
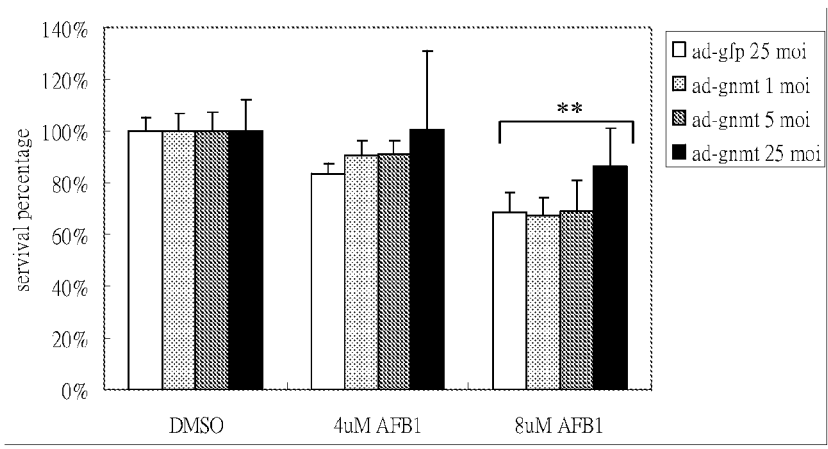
Figure 11:
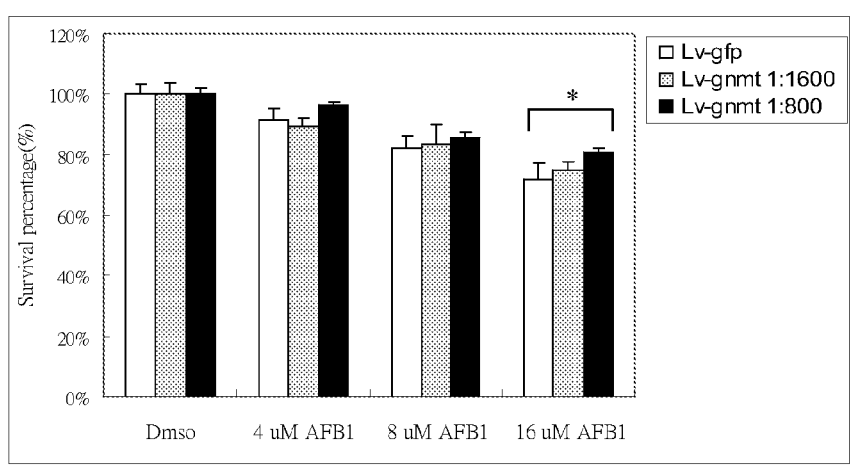

MTT assay was used to determine the percentage of survived cells. To optimize the condition of cytotoxicity assay, HuH-7 cells were treated with different concentrations of $AFB_1$ for series time course. As shown in FIG. 11A, the half lethal concentration (LC50) of $AFB_1$ was dependent on the duration of treatment. The cytotoxicity effect of treatment up to 16 μM $AFB_1$ was obscure within 24 hr. However, the survival rate of HuH-7 cells dropped significantly after 48 hr of treatment, even n the group treated with 4 μM $AFB_1$. The 72 hr LC50 of $AFB_1$ was about 12 μM. To determine the effect of GNMT on $AFB_1$ treated cells, we expressed GNMT in HuH-7 cells by infecting adenovirus carrying GNMT cDNA. Compared to HuH-7 cells infected with Ad-GFP control virus, the survival percentage of $AFB_1$ treated HuH-7 cells increased slightly but significantly by the dose of Ad-GNMT (FIG. 11B). Similar results were observed in another system in which GNMT gene was transducted via lentiviral vector (FIG. 11C). These results demonstrated that GNMT can antagonize the cytotoxic effect induced by $AFB_1$ treatment.

EXAMPLE 6

Inhibitory Effect of GNMT on $AFB_1$-DNA Adduct Formation

To determine the effects of GNMT on $AFB_1$-DNA adducts formation, we conducted a competitive enzyme immunoassay (EIA) was conducted to measure $AFB_1$-DNA adduct formation with antibody 6A10, utilizing a pair of stable clones from HepG2 cell line-SCG2-1-1 and SCG2-neg and GNMT recombinant adenovirus-infected HepG2 cells.

Cells were treated with DMSO and various concentrations of $AFB_1$ for 16 hr prior to DNA extraction. There is no obvious cytotoxicity effect during the treatment. The quantities of $AFB_1$-DNA adducts in SCG2-1-1 cells were reduced to approximately 50% of those in SCG2-neg cells (FIG. 11D). Furthermore, GNMT over-expression by GNMT recombinant adenovirus (Ad-GNMT) infection also reduced $AFB_1$-DNA adducts formation in a dose-dependent manner (FIG. 11E). Compared to Ad-GFP-infected cells, HepG2 cells infected with 5 MOI of Ad-GNMT resulted in a greater than 40% reduction of $AFB_1$-DNA adduct formation in both $AFB_1$ concentrations. It observed that a decrease of approximately 70% of $AFB_1$-DNA adduct formation in HepG2 cells infected with 50 MOI Ad-GNMT. Results were calculated by $AFB_1$-DNA formation quantity based on inhibition percentage. It indicated from the test data that compared to the control cells (SCG2-neg cells and HepG2 cells infected with Ad-GFP), the number of $AFB_1$-DNA adducts formed in GNMT-expressing cells was significantly reduced. It demonstrated that GNMT have a protective role in $AFB_1$-treated cells by reducing $AFB_1$-DNA adduct formation.

EXAMPLE 7

Generation of GNMT-TG Mice

Figure 14:
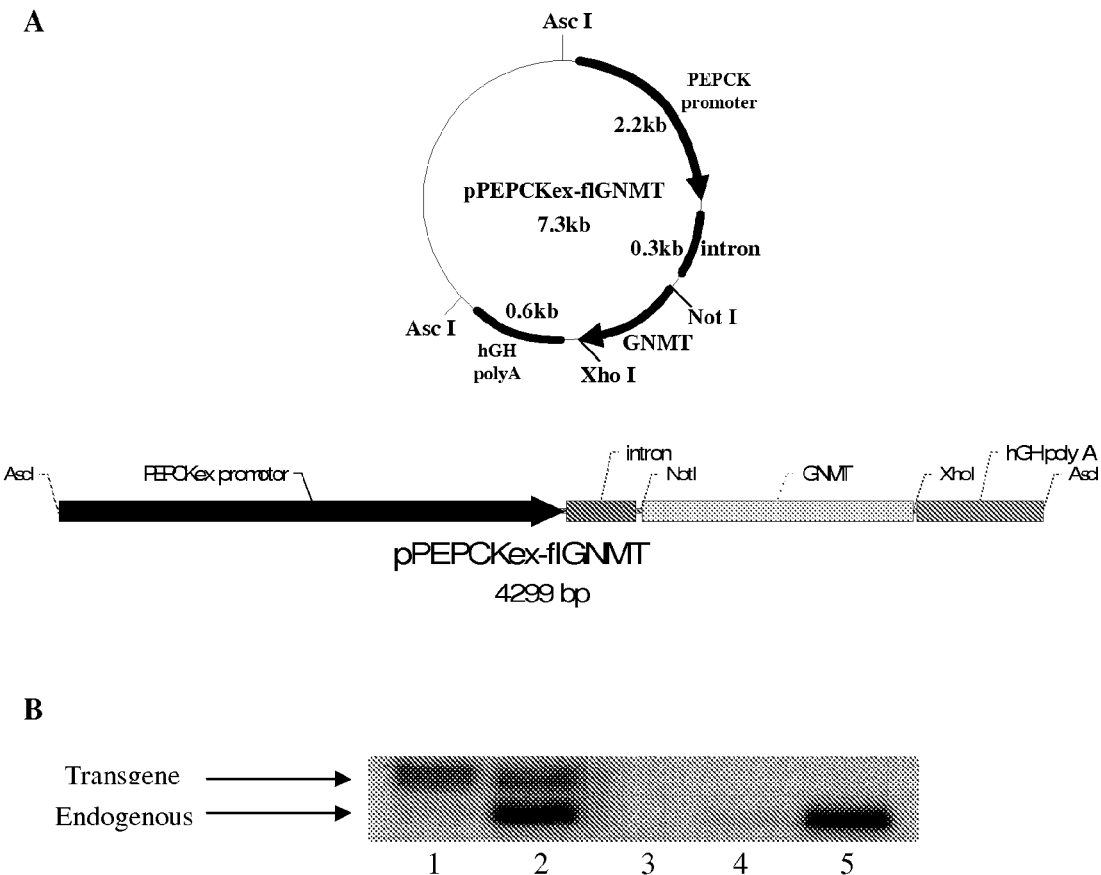
FIG. 14 shows a construction of the pPEPCKex-flGNMT plasmid. pPEPCKex (vector) and pSK-flGNMT (insert) digested with Not I and Xho I and ligated to produced pPEPCKex-flGNMT. B. The expression of the mouse endogenous and human GNMT mRNAs in various organs in the transgenic or wild-type mouse was determined by Northern blot analysis. 1) Kidney RNA of GNMT transgenic mice. 2) Liver RNA of GNMT transgenic mice. 3) Brain RNA of wild-type mice. 4) Kidney RNA of wild-type mice. 5) Liver RNA of wild-type mice. The result showed that GNMT transgenic mice expressed human GNMT gene (transgene) in liver and kidney.

In order to determine the effect of GNMT on $AFB_1$ induced carcinogenesis in vivo, a human GNMT transgenic mice (TG) model was established. The plasmid used to generate the GNMT-TG mice was shown in FIG. 14a. The pPEPCKex-flGNMT plasmid was constructed with human GNMT expression driven from the mouse PEPCK promoter (Valera, A. et al., *Proc. Natl. Acad. Sci. U.S. A* 91, 9151-9154, 1994). The GNMT-TG mice were generated by pronucleus microinjection of FVB fertilized eggs. Northern blot analysis demonstrated that the human GNMT was specifically expressed in the mouse liver and kidney (FIG. 14B), as expected.

Figure 12:
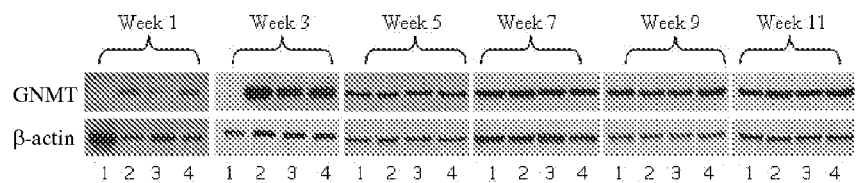
FIG. 12 illustrates the expression profiles and enzyme activity of GNMT in GNMT-TG and wild-type mice. A. GNMT protein level in 1, wild type male (opened diamond); 2, transgenic male (closed diamond); 3, wild type female (opened square) and 4, transgenic female (closed square) were determined by Western blot analysis (upper panel) and the quantitative data (lower panel). The result showed that transgenic animals have more amount of GNMT protein than wild type before 5 weeks old. B. Compared enzyme activity of GNMT between 1, wild type male; 2, transgenic male; 3, wild type female and 4, transgenic female.
Figure 12:
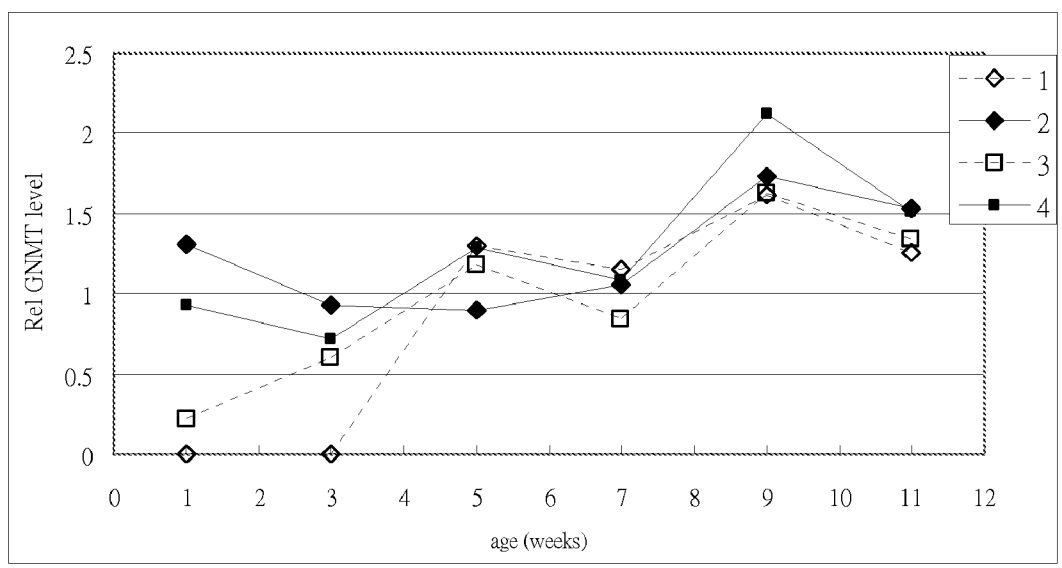
Figure 12:
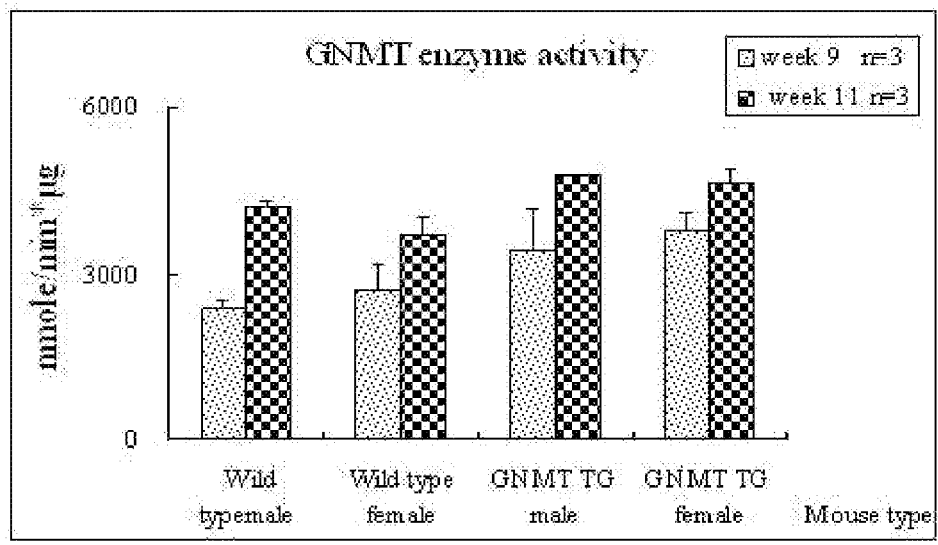

The expression profiles of GNMT in GNMT-TG and wild-type mice were determined by RT-PCR and western blot analysis. As shown in FIG. 12A, the mRNA expression level of GNMT increased by age in wild type mice, and came to the plateau at the age of seven week-old. The gene expression levels of GNMT mRNA in GNMT-TG mice were higher than the wild-type mice, specifically at 1 and 3 week-old. In addition, western blot analysis showed that the protein level of GNMT in male wild-type mice at 1-3 week-old was under the detection limit, while that was detectable in female wild-type mice at 1 week-old despite in a low expression level. By contrast, the protein amount was higher in both male and female GNMT-TG mice at the age of 1 week-old (FIG. 12A). These results indicated that the expression of GNMT in GNMT-TG mice is higher than in wild-type mice at 1-3 week-old. Moreover, we detected GNMT enzyme activity in GNMT-TG and wild-type mice liver lysate were detected. GNMT enzyme activity in GNMT-TG mice was significantly higher than wild type mice liver at 9 and 11 week of age ($p<0.05$) with one exception: male at 9 week-old (FIG. 12B).

In this test, GNMT-TG mice were not placed on the specific diet. The gene expression levels of GNMT in GNMT-TG mice liver were higher than in wild-type mice, specifically at 1 and 3 week-old (FIG. 12A), while it came to the plateau at the seven week-old.

EXAMPLE 8

AFB$_1$ Induced Liver Tumor Formation Blocked in GNMT-TG Mice

The GNMT-TG and wild-type mice were charged with AFB$_1$ intraperitoneally. Mice were sacrificed at 11 month-old. The overall incidences of pathologically confirmed hepatic tumors for male and female mice are showed in Table 8.

TABLE 8

The liver tumor formation of the 2 genotypes mice treat with solvent or AFB1.

|  |  | Gender | No. | liver/body weight % | No. mice with nodules | ALT |
|---|---|---|---|---|---|---|
| AFB1 | wild type | M | 6 | 4.7 ± 0.3 | 4/6 (67%) | 134 ± 112 |
|  |  | F | 21 | 4.0 ± 0.7 | 0/21 (0%) | 109 ± 97 |
|  | GNMT | M | 7 | 4.5 ± 0.9 | 0/7 (0%) | 61 ± 37 |
|  |  | F | 10 | 3.7 ± 0.4 | 0/10 (0%) | 100 ± 73 |
| Solvent | wild type | M | 6 | 4.1 ± 0.4 | 0/6 (0%) | 55 ± 23 |
|  |  | F | 7 | 3.8 ± 0.2 | 0/7 (0%) | 54 ± 16 |
|  | GNMT | M | 7 | 4.7 ± 1.0 | 0/7 (0%) | 48 ± 12 |
|  |  | F | 6 | 3.8 ± 0.5 | 0/6 (0%) | 40 ± 60 |

Figure 13:
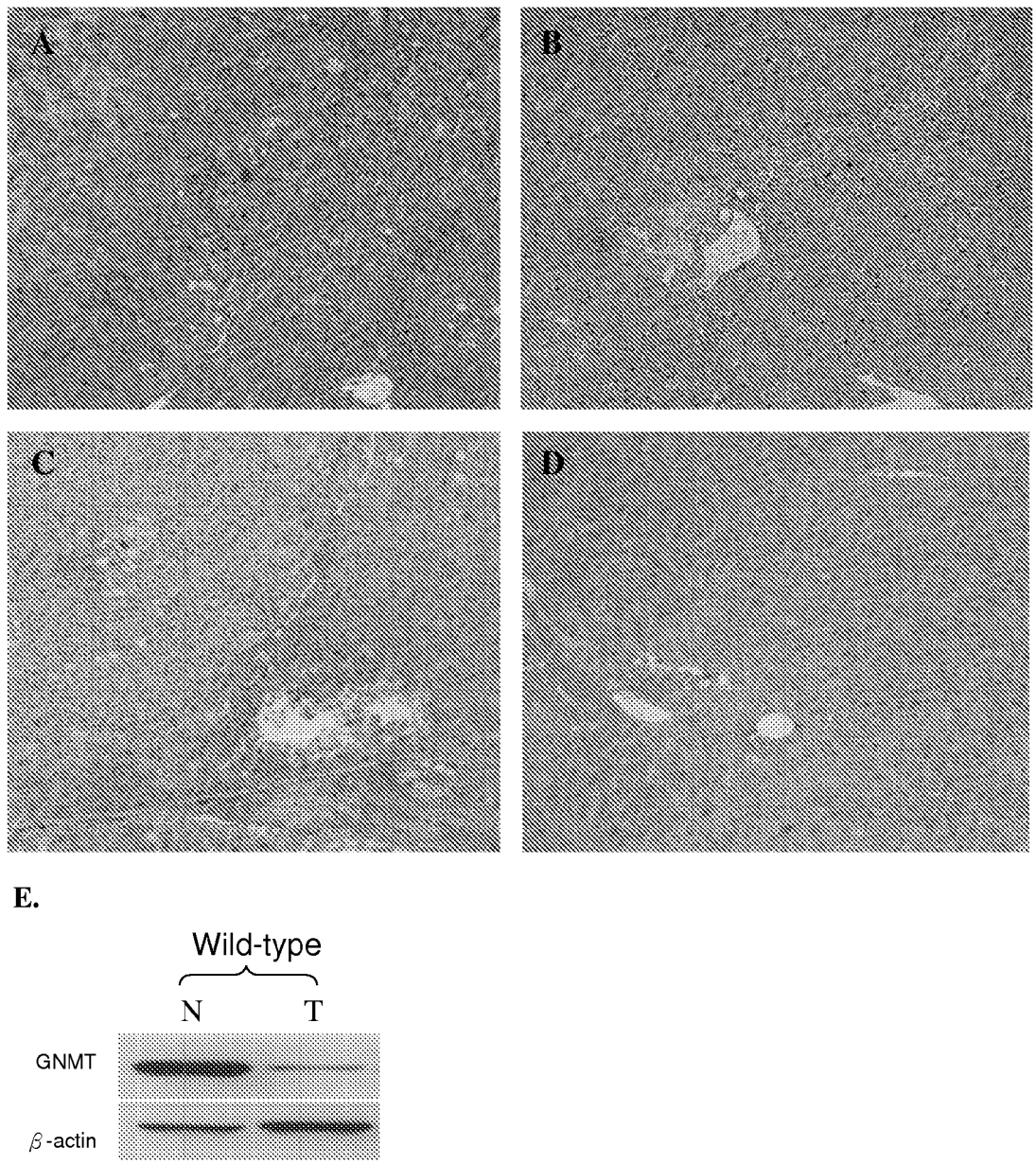
FIG. 13 shows H&E and IHC staining for the four groups of male mice livers. Photomicrographs of livers of carcinogen-treated mice by H&E staining. (A) Wild type mice treated with AFB1. X 200, (B) GNMT transgenic mice treated with AFB 1. X 200, Immunohistochemical analysis of the GNMT expression in the paraffin-fixed tissue. (C) Wild type treated with AFB1. X 200, (D) GNMT transgenic treated with AFB 1. X 200. (E) Western blot analysis of cell extracts from non-tumor tissue (N) and tumor tissue (T). The result showed that the GNMT expression level in tumor tissue was lower than non-tumor tissue in three groups of mice.

There was no liver tumor formed in both male and female GNMT-TG mice treated with AFB$_1$, while 4 of 6 (67%) male wild-type mice treated with AFB$_1$ developed hepatic tumors. No tumors were observed in mice treated with solvent (tricaprylin). Serum alanine aminotransferase (ALT) levels were measured in order to monitor liver function of GNMT-TG and wild-type mice at 11 month-old. The mean levels of serum ALT in the male wild-type mice were higher than male GNMT-TG mice in AFB$_1$ treated group, but there was no difference between the female GNMT-TG and wild-type mice. Pathological examination revealed the presence of dysplasia and HCC in the male wild-type mice treated with AFB$_1$ (FIG. 13A), while a normal pattern was observed in AFB$_1$ treated male GNMT-TG mice (FIG. 13B). Immunohistochemical staining demonstrated that the GNMT was expressed abundantly in the cytosol of the normal liver cells (FIG. 13D), while it was diminished in the tumor cells (FIG. 13C). This phenomenon is confirmed by western blot analysis (FIG. 13E) which is also observed in human HCC.

In the AFB$_1$ challenge experiment, the mice were injected with AFB$_1$ at the time that the expression of GNMT in GNMT-TG mice was higher than wild-type mice. The results showed that there were no liver tumor formation in both male and female GNMT-TG mice, but 4 of 6 (67%) male wild-type mice had liver tumor formation treated with AFB$_1$ (Table 8). In the example, the percentage of liver tumor formation in male wild-type mice was increase from 10% to 67%. At the same challenge procedure, the male GNMT-TG mice were no liver tumor formation. Moreover, though the level is relative low, GNMT protein is detectable by western blot analysis as early as 1 week-old in female mice liver. Those GNMT protein exerted a protective effect and prevented AFB1 induced liver tumor formation in female wild-type mice (none of AFB1 challenged female mice developed liver tumor). The test also demonstrated that GNMT can provide a protection effect against AFB$_1$ induced liver tumors formation in the male GNMT-TG mice.

Further, pathological examination confirmed that the liver tumor formed in the wild-type mice treated with AFB$_1$ is HCC (FIG. 13A). The results from immunohistochemistry staining and western blot showed that the expression levels of GNMT in tumor tissue were decreased (FIGS. 13C and E). This result was consistent to our previous findings in the human HCC. It also suggested that the regulation of GNMT during carcinogenesis in mice is very similar to those in human. Therefore, GNMT is helpful for the prevention of carcinogenesis.

What is claimed is:

1. A knock-out mouse whose genome comprises a homozygous disruption of the endogenous glycine N-methyltransferase (GNMT) gene and lacks expression of functional GNMT protein, wherein said disruption occurs within nucleotides 547-4875 of SEQ ID No. 8, and wherein said transgenic mouse exhibits increased susceptibility to liver cancer rates and develops fatty liver nodule and hepatocellular carcinoma nodule as compared to a wild-type mouse.

2. A method for screening a candidate agent for treating liver disease comprising:
   (a) providing the knock-out mouse of claim 1;
   (b) administering a candidate agent to said knock-out mouse, and
   (c) comparing liver function of the knock-out mouse to that of a knock-out mouse of claim 1 not administered said candidate agent; wherein an agent that ameliorates liver function is selected as an agent for treating liver disease selected from group consisting of hepatocellular carcinoma (HCC), glycogen storage disease, liver dysplasia and fatty liver.

3. A cell or cell line, which is prepared from the knock-out mouse of claim 1.

4. The cell or cell line of claim 3, which is an undifferentiated cell selected from the group consisting of: a stem cell, embryonic stem cell, oocyte and embryonic cell.

* * * * *

SEQUENCE LISTING

<160> NUMBER OF SEQ ID NOS: 8

<210> SEQ ID NO 1
<211> LENGTH: 29
<212> TYPE: DNA
<213> ORGANISM: Artificial
<220> FEATURE:
<223> OTHER INFORMATION: primer of PCR

<400> SEQUENCE: 1
gcggcggccg catgctggtg gaagagggc                       29

<210> SEQ ID NO 2
<211> LENGTH: 20
<212> TYPE: DNA
<213> ORGANISM: Artificial
<220> FEATURE:
<223> OTHER INFORMATION: primer of PCR

<400> SEQUENCE: 2
ttgcagtctg gcaagtgagc                                 20

<210> SEQ ID NO 3
<211> LENGTH: 20
<212> TYPE: DNA
<213> ORGANISM: Artificial
<220> FEATURE:
<223> OTHER INFORMATION: Primer of PCR

<400> SEQUENCE: 3
gttccttgcg cagctgtgct                                               20

<210> SEQ ID NO 4
<211> LENGTH: 20
<212> TYPE: DNA
<213> ORGANISM: Artificial
<220> FEATURE:
<223> OTHER INFORMATION: Primer of PCR

<400> SEQUENCE: 4
cggccacagt cgatgaatcc                                               20

<210> SEQ ID NO 5
<211> LENGTH: 30
<212> TYPE: DNA
<213> ORGANISM: Artificial
<220> FEATURE:
<223> OTHER INFORMATION: primer of PCR

<400> SEQUENCE: 5
gcgctcgagt cagtctgtcc tcttgagcac                                    30

<210> SEQ ID NO 6
<211> LENGTH: 20
<212> TYPE: DNA
<213> ORGANISM: Artificial
<220> FEATURE:
<223> OTHER INFORMATION: primer of PCR

<400> SEQUENCE: 6
gtggggcgcc ccaggcacca                                               20

<210> SEQ ID NO 7
<211> LENGTH: 24
<212> TYPE: DNA
<213> ORGANISM: Artificial
<220> FEATURE:
<223> OTHER INFORMATION: primer of PCR

<400> SEQUENCE: 7
ctccttaatg tcacgcacga tttc                                          24

<210> SEQ ID NO 8
<211> LENGTH: 14777
<212> TYPE: DNA
<213> ORGANISM: Lambda phage
<220> FEATURE:
<221> NAME/KEY: misc_feature
<222> LOCATION: (5953)..(5953)
<223> OTHER INFORMATION: n is a, c, g, or t
<220> FEATURE:
<221> NAME/KEY: misc_feature
<222> LOCATION: (13551)..(13551)
<223> OTHER INFORMATION: n is a, c, g, or t

<400> SEQUENCE: 8
tctctgtgag ttcaaggcca gccaagacta tacagagaaa ccttgtctca aaaacaaac    60 aaacaaacaa acaaaatgca ccaccatgcc tggttcccca gttttaaaaa ccctaagtaa  120

```
ataaaagata ccacttaaga tgctgagatg agatttgaaa aaagtctagg attgataggt    180 ttaccccccca aatgctttga tatgtggcat tggatttact tgaaattccc aaatacagtt   240
tctcctctct gctttgtctc cacagggact gatgtagccc agatttgcct tgaagtctat   300
gtaccctaga atatctttga actccagctt ttctgttctc agctgccaag tacaggactt   360
acaggcacac accatcacac tcagcctcga gaatctttct gagcatagtg tcagaggcct   420
gtgtgtaggg acattgagtc cccaagactg agcctggtca gaaccatttg agattggcgc   480
tgtgctaaca aaagttttaaa aatgtgggct ggagagatag gtcagccatt aaaagcccta  540
tctgcagcta gggtcgtagc gcacactttt agccctagcc cttgggaggc agaggcagtt   600
ggatctctga gttcgaggcc agcctggttt acagagtgaa ttctaggaca gccagagaaa   660 cccttctca caaaaccaa accaaaccaa acaaaccact tggtcctctg tggggttcag     720
tgtcctcagc accacccagt ggctccccac tgtctacaac tgcaggttca gggtatctga   780
agctctcgat tctgggctcc atgggcgtca gacacatact gacatctatg aagtcaaaac   840
agccataccc actataagaa ggttaagtca cacaactgtg ggcctccttc catctccagg   900
gttcaccctg cattgggaag gcgaagggcg ggcgggcggg cgggatgctc cctgtcttct   960
ctcttctttc cacgtaacga gtgttcacag agttggaagt gtgtgggcag gcggggcagg  1020
cggggcaggc ttctcgttgc tcacacgcat cttccagagc cgactttagc ccggctggga  1080
tcttgtcctt ggtggggtaa aaagggtgag cgggtaacac gaaacggacc ctcaggttat  1140
acagtgacgc tagcccgagc gggcgccatg agcaccttcc ctgccgaccc ccaactttcc  1200
tctctgaagg tgctcccatg gaaagcagat ggaaggcttg ctatgtctcc cacattgttc  1260
actaattcat tgagcactaa taatcctcct gtctcacctt actacaccca gcctttaaga  1320
gattgcagag tataaagccc atggattgga aggcccaggc taccttagga ggctcctggc  1380
tggtatgggg gaggggaaga gagacacgcc tatctccagg tgtactcttg tacttggatg  1440
agcatctttc tcaaagactg ttcataatgt cccgacacag tggctctctt tagcggagtg  1500
ttccctccac taaatgataa gcagtgttgt gtagacactg tgctgggctg ggcatgtaat  1560
aattctgttt tgggtggatt tcaggcttct tccccttcct ccttgggtag gggtggagtg  1620
atctctcatt gctttacttt tgtgagttcct cccggccacc ctggcgagtc ctatctgacc  1680
tgtcttacta agccaggtcc aggattgctg tgctgagcca tcctcaaggc agaggcagca  1740
agcctggctc tgggcccagg gcccagcagg ggcgtgtccc tgctctcacc tgccattggc  1800
caggtgggac tgccttgcca gaggattata agtgcggatc gcgtggcctg agagccaggc  1860
gccggtcagg atggtggaca gcgtgtaccg tacccgctcc ctgggggtgg cggccgaagg  1920
gctcccggac cagtatgcag atggggaggc cgcacgtgtg tggcagctgt acatcgggga  1980
cacccgcagc cgtaccgcag agtacaaggc gtggttgctt gggctgttgc gccagcacgg  2040
gtgccacagg gtgctggacg tagcctgtgg cacagggtga gtccaaacgg gccggcctgc  2100
ttaggccagt ctgggcagcc tctgcgggct ggagcctggc aggcagtact agggggtcaa  2160
gagcccttgc tcatcagggt agtatgggca tgggagagca tctgccgaga aacagtgcgg  2220 gaagggggcca gggtgtgcgc agagaagtat tcatgggaca gagcaaaatc cgagctttgg  2280
gtcaaggtgg atccttggct ccggcgctgt tcctcctgcg attggcctct ggcagtgtga  2340
acagaacatt tgtagcacgt ttgcacagcc aagtgctgtg ccaggagttt gggtacgtgt  2400
gttgcaagct gtaacaaaac cccacgaggt gagcagcgct tttctccaac cagtagtact  2460
aaagaaaaag tcatttccaa gaggtaaaag gcccccattt ggtggagagg atacagacca  2520
```

```
ggatagtgtc tggcccacac tcccgactca gcccagaact cacgcacacc tctgattgag   2580
ttatttccag gagcaccagt atgccaggtt ctcaagtgca cttttgtaga atgcctgact   2640
atgatttaaa aacaaaaaca acaacaaaaa gccattgagc cggtgagatg gtccgactac   2700
taagagcccc ttaggctctg gcagaagaca ggctctcagt gcctagcatc tgcatcaggt   2760
ggctcataat cgcctggaat tccgttccag ggggaggtta gcgctccctt ctggccgtgg   2820
agggcactgt actcacatgt actacacata cagacataat taaaaataaa aaatgtgtt   2880 gatgtcagga gtagtggcac atatatttaa tcccagcact cagggactcc taaataggtg   2940
gctctctgtg agttccaggc cctgcagggc tacattagga gaccctgttt ctaataagag   3000
gcagctgggg agatggcaca tgttcttaca gaggacccaa atttggtgcc cagcaccctc   3060 tctgggtct gcagacacaa ggtatgcaca tgatgcacat attcaggcac gacacatgaa    3120
attaaatttt gaaaaaaat ttttttgaaa cagaatctct ctttgtagcc ccagctgtct     3180
tggaactcac tgtttaaacc aggctaaaaa aaaaaaaaa aaaacaaaaa ctctcaaaaa   3240
aattttttgc tacctgataa ggaaaattct ttttttttt taaagattta tttattatta     3300
tatgtaagta cactgtagct gtcttcagac acaccagaag agggagtcag atcttgttac   3360
ggatggttgt gagccaccat gtggttgctg ggatttgaac tctggacctt cagaagagca   3420
gtcgggtgct cttacccact gagccatctc accagccccc aggaaaattc ttaatgggtc   3480
acttgagacc agtagagatg gcctgggaca ggaagcagag gaacggactc tggaatgtta   3540
tgtctgggga aatgtcacac acatttggcc tcccaggctc ctctgactgg tcctctagtc   3600
ccccgtttct gacctcatcc agagtggact ccatcatgct ggtggaagag ggcttcagcg   3660
tgatgagcgt ggacgccagc gacaagatgc tgaaatatgc gcttaaggag cgctggaacc   3720
ggaggaaaga gccatccttt gacaattggg gtaaatctgt ctgtccaggc cccccagaca   3780
tgcacctcca gggtcactct ctgccctggc tctctcttgc tgtggagctg aatggttttt   3840
cctcagtgca cggtacagtc cctgtcaact tcctaaaaag gaaggctttg gcatcagagt   3900
aggattccgg ctggtaagag caagtttgtt gtatttatgg tgctaggcat tgaacttggg   3960
catgccaagt agacccttga tcactgggct gcattaccag cggttttat gcttttcccg    4020 tgttgcctgg cttggctaag ctagatttaa gtgatgctcc tgtctaacag agtctagagg   4080
tgtacgtcaa gtcactgggc cctacagagc tactttaac tgtcttatca catcctgtct    4140
ctcctcccta caaaagcccc taagtggagg gctggctttg ccaactgtgg ctctctccat   4200
ccctaatgag tccccatgtg tctctgggag gaggtggttg cttctgtgct gtgctataat   4260
tctcgactcc ccccccccaa cccctgccct ggcctccagt cattgaagaa gccaactggt   4320
tgacgctgga caaagatgtg ctttcaggag atggctttga tgctgtcatc tgtcttggga   4380
acagttttgc tcacttgcca gactgcaaag gtaagctggt ggccttggct gtggctcttg   4440
ccttgagctt tcccacgtcc gaagatggct ggcctgctgc cctgataagg cagacctgca   4500
ttttgcctgt cttctttagt gctggcactt gggagggaga caggggcggg aggtggtgct   4560
ggaggcctaa gcagatggtg tctgtggccc tgccgggaac ccaggtgacc agagcgagca   4620
ccggctggca ctaaagaaca ttgcaagcat ggtgcggccc gggggcctgc tggtgatcga   4680
ccaccgcaac tacgactata tcctcagcac aggctgtgcg ccccggggga agaacatcta   4740
ctataaggtt gggctgcccc caatgggaa gcgggagctg gagggccaga agccccgtgg   4800
tggctcaggg aatgacgcaa cccatgccct cagagtgacc tgaccaagga cattacgacg   4860
```

```
tcagtactga cagtcaacaa caaagcccac atggtaaccc tggactacac agtgcaggtg   4920
ccaggcactg gcagagatgg ctctcctggc ttcaggtatg acgtggtttg gcaggagaga   4980
ggtggtggtg gtggggagac ctgaggccag cagccctcat atctggctgg ggcectgtt    5040
gcagtaagtt ccggctctct tactacccac actgtttggc gtcrttcacg gagttggtgc   5100
gagcagcctt tggggcagg  tgccagcaca gcgtcctggg tgacttcaag ccctacaagc   5160
ctggccaggc ctacgttccc tgctacttca tccatgtgct caagaagaca gactgagttt   5220
ctccggctcc cagaagccca tgctcaggca atggccccta ccctaagacc atcccctaat   5280
gcagatattg catttgggtg cagatgtggg ggtcgggcaa acgagtaaaa caatacagtc   5340
tgcattctcc aagcctgtgc ctggtgtttc ttcagaagta acgtgttttt atggtgtccc   5400
ccccccccaa tcccccctca agacctcagc ctcccataac cttgccttt  gcaccgcaac   5460
ctctcacaag accagtagga ggcagtatac actttatttt ctactccaga actagtgtct   5520
ccgcacaggt cacaggctgc caagccccta gctgccagcc ctgcctctcc tcctgagcac   5580
taggggcccc cactagggct cacaagggat ctctgggagg aggcagcctt caggcgacag   5640
gcgggaggta ccttcagtca gggggcatag gcagacggca ggcaggcagg caggcaggca   5700
gctcctagca ggctgcaaac ttgcgttgga tgcgcttgta tcgcaacagc tcctgctcac   5760
tgactgaggg ctgcagccgg gctgcggcct gcaacaggtc ctccatggtg agcagcagtg   5820
ctgagctccg cagctctagc cctaagggt  ggaaaggaag actaaggcca gagccccagc   5880
cctagctgaa gtacagaggc tgcagtctat gcctaggtag gagagccact ccggggggg    5940
gggggggggg acngcacggg acgacgacga acgacacccc ctgctcagcc attcctctgg   6000
aattcagggc caggactgtc tccctagctt tatggttccc atccagggct ggcaggtggg   6060
ctcaccttcc tctaggtctc gaaccctgcg tttgagggca gtcatcatgg cgtcagagca   6120
gagagaatag agatctgcac cagtcagctg tgggtgggca gcaatccagc acgtttgcca   6180
ggctcacaga gggctccagc ttgaacctat cacacccaca ccagggatgt taaagctggc   6240
ctcacctcct ccctcagaag tcatgatgac tcgcacacat cccctaactg tctaagcccc   6300
caccccagct ctctgactac gcatacttcc gtgtgatggc gctcagcaca cgcagctggg   6360
aggcccggtc ctcactcgcc cctacaaaca ccagcttgtc aaatcttcag agagacagag   6420
acaggaagtg ttagggctgc caaccatgag aggtgaagga tgcccaggat agaggttaag   6480
gcgcaaagga gccttgtgga ggggagaggt ccagggtccc tacctgccag gccgcagaag   6540
ggcagggtcc aggaggtctg gtctgttggt ggctccgatc acaaacacat cctgggtgct   6600
gtggagccca tccagctcgg ctaggagctg agacacaact ctgtacggga ggaaggcggc   6660
aaaggttgca gagtccttgc tgtgccctca ggccagctgc gcttctcttg aagactgctt   6720
cagcaaggtc ccttgctaag ctctgcccca tgtccctgcc acactggtga gcctcctcaa   6780
agttccccac tccttttag  cttcccttct agctctgaac tagaagggca ggaacctctg   6840
tcttagaggc ctgggctgga gactgatgtg actcaagata tatacacaga catatataca   6900
tatacgcata tatacatatg tatatgtgtg tgcatataca cacacacaca catacacaca   6960
cacacatatc tcatatccct ccccagactc cagaacccct gacctgtcca tcaccctcc    7020
agaatctcca ctccgtccgc ggcttggagc taaggaatcc agttcatcaa agaagatgat   7080
acagggagca gcagccctgg ccctggcaaa cactgagaaa gaggctcgca ggagagtggt   7140
gtcaaggagc ttcaagtcag gggagaagga tggcacatgt gcccgacagt tcctccccgg   7200
ccattgccca ctgagctgac caggagcagc cactggggaa gatggtgttg gggaagggcc   7260
```

```
cgagactcgc tcgctctccc cgctcactca ctcaccttcc cggacattct cctcgctttg   7320
gcccacatac atgttgatga gctccggtcc ctttacactg agcagtggga tggacggaca   7380
aatgagaccc atcagacgtg ctgtcctccc ctccccctccc accacctgcg acaactcccc  7440
tccccctttc tgcaccggct acagctccca gcctcccaca tttctcccca gccctgccaa   7500
cctgaggaag gtgaggctgc actcagtggc tacggccttg ccagcaggg tcttgccagt    7560 gcctgggggc ccatggagca gaaggcctga tcgtcttagg cccaggctga gcagctcagg   7620
gtgttccaga ggcagctgga tggtttctag gatctccttc ttcacatcct gcagcccgcc   7680
cacgtcgtgc caggacactg aagggatcta aagacggac cagtggtcag ggacgtgtca    7740
gcagagagag cccttgcccc ccccccccc acggaccag gattctcacc ctgggtgctc     7800
ccacagcttg ggagtgagct gtctgcagtt gatctaatgc ctgcccgaag tcctcagcca   7860
gcaaaggaaa gccagccaca cacaggtccc cctcatcctc ctcactcaaa ccacctgccg   7920
agctgcaaag aaacacgatg gggggaggg ggtaggctta cagctgtacc ctcagcatct    7980
gggaccagca ctcatggggc agaggcaggt gatctctatg agtccaagac tagcttggtc   8040
tccacagtga gtccaggcca gccaaagact acatagtgag tccctgcctt aaggataaaa   8100
aaggaccggg ccaatcaggg tatggattaa ggctctaaca aacgagagac agagagagag   8160
agagagagag agagagagag agagagacag agacagagag agagagacag agacagagag   8220
agagagagag agagagaccc cctctctagc agggtcccat tgccttccca gccacctggg   8280
atgagtctgt cttaccccga ggctctgatc ctggtgcagg ctgcccggca ggtatgggtc   8340
agaagggcat agaggtcccc caccacaaag ccctagggag ttacacaaaa ggacacatgg   8400
gtagggcagg gcacaggagg cagaggccaa gtctggcttc cagctggagc agaggctttc   8460
gtggtttcca gtctcacggg gcagcagaaa cgaggccctg tgtgacaggg accctgtgac   8520
ggcatagtgt caaggcccct gtgcagacac tcaccgcaca gcgccgtgcc agctggggca   8580
ggttaacctc ctggcctaag ggaaggtggg cagtgagggc ctgcaggata ctgagccgtt   8640
gagcctcaga cagcactggc acctctagct catgaggaaa tgccgtctgc acatcggtgg   8700
gcaggtcctg gacacggctt gtggtagcca ccaccatgag aggagggcac ctgcagacag   8760
ggacgtgggc aaggtctggc atggctggca gctcctgcct ttggtgtgca ggaatgggga   8820
gggttggtgt caggactggg tagggatggg catcatccag agtccattat cccctgatgg   8880
tggggacacc atgaagggag accctgcttc acacggggg ggggggtgct cactgggac    8940 aaaagcttca accttgtgtt cccttcaaaa tgttcaacct tgtgttccct tcaaaatgct   9000
agaccgcacc ctcctacctc tggacactgt aaattggccc caaggacagg taggtgagag   9060
ttctgagaag ctagcagggt gtgaggaatt gagggctgaa tagggggtt cccttcataa    9120 cctgcctgct ctatacatac ctgctgagag cgtcctcatc aaggaggaga tgacggagtg   9180
tggccgcaac acgggcatcc tcacccagtc cgtctcggtc ccggcccagg aggtccacag   9240
ctgtcaagag gaggactgca ggcctgcagc ggtgggcccg ggagaaggtg gcctgcagct   9300
ttgtctccac ggccctactg ctgtctgcac agaggctgga gcagggcacc tggggaagag   9360
accagatggg tcagcatgaa gggagaaggg tgactaggcc atctttgtga gtagggacag   9420
gtgaaggagg gaccctggcc aggtgggagc tttggttcac cctatccttt gcctggagtg   9480
tgcagccttg aaacccctcc ttcctgagag gagctctgag tagctgagca tcaagggggct   9540 gtatactggc ctgaccactg ggcgagctct gagtagctgg gcatcaaggg actgtacact   9600
```

| | | | | |
|---|---|---|---|---|
| ggcctaacta | ctgggctgaa | gcattagggc | tgccaaatgg | taatgaggga acccaggaga | 9660 |
| agagagagca | aggcagagtc | tgagctcagt | ggaagcggct | ggggctcgtg ccagaggcct | 9720 |
| tcaccttcag | caaatggagc | ccaaggcggc | tgcatgcagc | cgtgacggct gtggtcttcc | 9780 |
| cgctgcctgg | gggaccctgc | agaagcacac | agctggttcc | tgtgagcaat gttcctctgc | 9840 |
| aattagagaa | tagatattgt | ctcccatttt | tctgcccaaa | tgttaagacc ctagtaagac | 9900 |
| agggacccct | ggatttcata | agtgtcccat | ctctccttgt | gcctccctaa cccccatcca | 9960 |
| ggcagtgtcc | acagtccgag | gccttgtgtc | atgccatctc | tggtgcccgg cagaagcac | 10020 |
| tgagaacatt | ttgcagccgc | agaccagtta | gccttcagtg | aagcccagct ggataggtct | 10080 |
| ggatctagac | ttgggccact | ggagtggggc | actctgctct | tgggagatg tagtgggaaa | 10140 |
| ggccaggacg | gatctcgggc | tcccaagca | gaaaagcagc | tttaggatca gctgctgggg | 10200 |
| agtctgcttg | tgtaagtggg | tagcctgtgg | cctggactgg | gggcctggct tgtggatccc | 10260 |
| cgacttgggg | tagactactg | gaagtaattt | ccccggatgc | tgctctacag agatgctctg | 10320 |
| agcaggcccc | tctcacggcc | cgaattcaca | cctcccggcg | tggcctcact cacccgggct | 10380 |
| gcaggtgagc | cttcaggata | gcacacagct | catttaccaa | ggcctccagg cctggaggag | 10440 |
| acaagctgtc | ccagggtggg | gaccttcctg | aaggcagcga | tggcacatga ctcagggcgg | 10500 |
| tgccagcctg | tgaaagcagg | aagcccagca | aggttctaca | gggtccctac ccctttgacg | 10560 |
| ctctcctccc | aggaacccac | ggccttacca | ggtataaaga | ggtgtgggtg gtatcagcca | 10620 |
| gaaaggcact | ggctggcccc | tctggggctt | ctccaaccgt | tttcttcact ttgaaaaaca | 10680 |
| tctcccgcca | cctgtaagaa | aggagggtca | gggaaccagg | accgagcgtc cacatgtgca | 10740 |
| cctcttgggg | agtgggtagc | tttctcacag | aggaccaact | taggagccct gagactgatg | 10800 |
| aggcaaggcg | gggcccccag | agggctgggc | agggaggaag | tgggggatac agaagggcag | 10860 |
| cccctcatt | acagccatca | aatagcccag | gaagggcatc | tctctggcca tatagcctag | 10920 |
| ccacctactc | taaaaggtga | agccaccatc | attacacaca | gcaacctggg gccgtttccc | 10980 |
| tcagtttctg | aacagtctct | ccctcctaca | gatcttcacc | caccagggtc ccagatctca | 11040 |
| gacacaagtg | tcccttcatt | tttattcaac | aattcaacta | attctaacta aagttagagt | 11100 |
| ctttaatcat | ggtgtctaac | tctagtcctg | gggagttgag | gcaggcggga aggtcttaag | 11160 |
| acagaccagg | ctgggctacg | aagtgagagt | gattctctgt | tccagaatta cctgtgaagc | 11220 |
| ttgcttaatt | aattaattaa | ttgtatacga | gtcttcagac | acactagaag agggtaccag | 11280 |
| acctcattac | agatggttgt | gagccaccat | gtggttgctg | agaattattg aactcaggac | 11340 |
| ctctggaaga | gcagtcaggt | attttgtttt | tgttttccgt | ttttttgaga cagggcttct | 11400 |
| ctgtatagcc | ctggctgtcc | tggaactcac | tctgtagact | aggctggcct cgaactcaga | 11460 |
| aatccacctg | cctctgcttc | ccaagtgctg | ggattaaagg | tgtgtgccac cccgcccgg | 11520 |
| cttgagcagt | cagtgcttaa | ccactgagcc | atttctccag | ctcccttgtg aaactttaaa | 11580 |
| aataagtata | tttcatgcat | tctgtgagtc | cactcaacag | gctggtgagt gccaggatca | 11640 |
| ggggacaagg | caagaatgag | gggtgactg | ttagtgccca | tggtttgtgt ggctaggaga | 11700 |
| gctaaagaac | cagagctatc | tgcaccctcc | tgtacccacg | gcaaaccctc tgagccgtgc | 11760 |
| cactcctgta | cccacggcaa | accctctgag | ccgtgccact | cctgtaccca tggcaaaccc | 11820 |
| tctgagccgt | gccactcctg | tacccatggc | aaaccctctg | agccgtgcgt acacttgttc | 11880 |
| attctggaag | atgtacactt | gttcattata | ggagacattt | aatgtctcct agaatagact | 11940 |
| caaactcata | acctcaaaag | tttagaagag | gctcaagtgg | tggtgtaaac cctgaatctc | 12000 |

```
aacactctgg aggcagaggc aggaggatct ccgtgaatcc gaggccagcc tggtttacac   12060
agcaagttcc aggaaagcaa ggactacata gaaagaccct gtctcagccg ggcagtggtg   12120
gcgcacgcct ttaatcctag cacttgggag gcagaggcag gtggatttct gagtttgagg   12180
ccagcctggt ctacagagtg agttctagga cagccagggc tacacagaga aaccctgtct   12240
cagaaaaaag aaaaggaaa gaaaaagaa aaagaaaag aaagaaaaaa gaaagacctt     12300
atctcaaatt ctcccacccc caaaaaagtc taagaggctg aatcatcatc acacacacac   12360
acacacacac acacacacac acacacacac acacttactt caaacattaa tgctggggcc   12420
acccagatgg ctcagtaggt aaaggcactc gctagcaggc ctgactacct gagttcagtc   12480
ctgagaattc atagggtagg agcgaaccga cgcttacagc tcgccttctg acctctgtaa   12540
gctgctgata cacattttt tcattcaaga taggtatttc tctgtgtagc cctggctgtc    12600
ctaatacttg ctttgtagac cagactggct tcaaattcat agacatccac ctgcctgtac   12660
ctccagagtg ttggaattaa aggtgtgtgc caccatgcct gtcccaatac acattttata   12720
aattaaatgc aattttagc aaaataagct ggatggtagt ggcatatgcc ttttcccccc    12780
acattaactt atttattcac tttacattct gataacaggc caccttctcc acccagtccc   12840
ctctcataca gcttctccac tcaaccccct ccccttctcc tctgaaaagg aggaggtccc   12900
ccttgggttc caatccaccc tgacatatca agtcactggg tggcgcacac ctttaatcac   12960
agcactcagg aggcagaggc aggtgaatct ctgagttcaa gactagattg gtctgcagag   13020
tgagttccag gacagctagg gctacacaag caaaccctgt cccaaaataa aaaaatagaa   13080
tataagtaat aataataata atgatgataa tattaaatac tacatcatcc tttgaaagga   13140
aaagatggca caagccctag tttcatctcg attctatcta actggtgtgg ggtgtgactc   13200
tgtattacat gcagtctgga agcacagcca gctgagcggt tattaaccag cagcacggag   13260
actcagagat atttacgcta ctcactcgga agacggtaag tgcatgtagc agccagtaac   13320
ttaatctcct agagacatca ctagatagag ctccttaac tcctcggcag ggagacacca    13380
tggaacagag cacactgtag gcctctctaa gacccaccag gccgggcagc acgcctttaa   13440
ttccagcact tgggaggcag aggcaggtgg atttctgagt tcgagtccag cctggtctat   13500
agagtgagtt ctaggtcagc cagggttata gagaggaacc ttgtttggga naccccaaaa   13560
aaaaaaaaaa aaaaaaaaa aaaagaccca ccaggatgca aactctttta cttaaaatgt    13620
tttagttgcc attggcagca acagtggctt caaagtagac aaaggttttt gttacaaaat   13680
tcttgtaagt tgggctgggg agatggctca gctggtgaag tactacccaa acaagtatga   13740
agagcagtgt tcagcatcct agaaccacag aaaagatgcc tgtatgacag cctgcccatc   13800
atcccagcaa gcacggaagg agacagggaa tgaccagggc aagctgtcca cagagtgaga   13860
gaccctgctt caaaatgcag tcagagtgca gttgaaggca ctgatatcca ccaccatggg   13920
gcctccaggt gtgcatctgc acacccatgc actcacgctc acaaacccaa aatggatttc   13980
ctctgagtta ttccagttgg cagtggctgt ggttaaaaac taaatgtaa ggagaaagat    14040 gcacagtgca tgaagcctag agcttggtgc gcaacagggg aaagatgcct gtgagctgtg   14100
ctctagctca gaaaaccacc tcattgtggc ttaggtaggg tacagcctcg tgcctctatc   14160
aagcatcctg tcggaacatt ctggaagcac tgcatagga agcaatgagg cgcagctctg    14220
agggaagtta cgaaggaacc accttcttca gtaggggatt ggtgctccac ttcagagagc   14280
agaaaggcca gtaatctaga ccctaccaca gccctgctga gggagcaggg gccagagccc   14340
```

```
                                              -continued
ggtggggcac acagaagagt tgtgactgtc tgcaaagtag ctttggtttg tgaagcagag    14400
tacagaggac gctgaagagg gtccaaccat gatgaaactc ctttctaggg aatataagat    14460
ctctgggttt cccttatcaa gtctgagtgg actcagcggt ttacggtacc gagcctgcta    14520
ggcacccaga ggtgggcagg tttcaggagc tgggtcagca gcagtgctga aaatggcctg    14580
ctgtgtctca gaatgcctga tcacctgttt ttctttgtgg gcactaagtg tgggaggtct    14640
gcaggtcttc tacagaaaac aaagtgaggg actgttggta gaatgactgc ccagctccta    14700
aaagtcttag gactcagatg gtaggtagaa gcaggaaggt cagaagttca aggccatcac    14760
tcacacagat tttgagt                                                   14777
```